US009968665B2

(12) United States Patent
Boyd et al.

(10) Patent No.: US 9,968,665 B2

(45) Date of Patent: May 15, 2018

(54) ANTI-MALARIA COMPOSITIONS AND METHODS

(71) Applicant: ARTIFICIAL CELL TECHNOLOGIES, INC., New Haven, CT (US)

(72) Inventors: James Gorham Boyd, Madison, CT (US); Thomas J. Powell, Madison, CT (US)

(73) Assignee: ARTIFICIAL CELL TECHNOLOGIES, INC., New Haven, CT (US)

(*) Notice: Subject to any disclaimer, the term of this patent is extended or adjusted under 35 U.S.C. 154(b) by 0 days. days.

(21) Appl. No.: 15/264,035

(22) Filed: Sep. 13, 2016

(65) Prior Publication Data

US 2017/0128558 A1 May 11, 2017

Related U.S. Application Data

(60) Provisional application No. 62/219,260, filed on Sep. 16, 2015.

(51) Int. Cl.

| | |
|---|---|
| ***A61K 39/00*** | (2006.01) |
| ***A61K 39/39*** | (2006.01) |
| ***C07K 7/08*** | (2006.01) |
| ***A61K 39/015*** | (2006.01) |

(52) U.S. Cl.

CPC .............. *A61K 39/015* (2013.01); *C07K 7/08* (2013.01)

(58) Field of Classification Search

CPC .................. A61K 39/015; A61K 39/39; A61K 2039/5555; A61K 2039/64; A61K 2039/6093; C07K 7/08

USPC ....... 514/1.1, 2.3, 2.4, 3.3, 3.7, 4.4; 530/300

See application file for complete search history.

(56) References Cited

U.S. PATENT DOCUMENTS

2016/0324958 A1* 11/2016 Burkhard ........... A61K 39/0013

FOREIGN PATENT DOCUMENTS

| | | | |
|---|---|---|---|
| WO | 2004014957 | A1 | 2/2004 |
| WO | 2010115229 | A1 | 10/2010 |
| WO | 2012035558 | A2 | 3/2012 |
| WO | 2015104352 | A1 | 7/2015 |

OTHER PUBLICATIONS

DeHaes et al.; "Polyelectrolyte Capsules-containing HIV-1 p24 and Poly I:C Modulate Dendritic Cells to Stimulate HIV-1-specific Immune Responses"; Molecular Therapy; 18(7); pp. 1408-1416; 2010.

International Search Report and Written Opinion; International Application No. PCT/US2016/051469; International Filing Date Sep. 13, 2016; dated Dec. 9, 2016; 13 pages.

Onda et al.; "Sequential Actions of Glucose Oxidase and Peroxidase in Molecular Films Assembled by Layer-by-Layer Alternate Adsorption"; Biotechnology and Bioengineering; 51; pp. 163-167; (1996).

Parra-Lopez,et al.; "Major Histocompatibility Complex and T Cell Interactions of a Universal T Cell Epitope from Plasmodium Falciparum Circumsporozoite Protein"; The Journal of Biological Chemistry; 281(21); pp. 14907-14917 (2006).

Volodkin et al.; "Matrix Polyelectrolyte Microcapsules: New System for Macromolecule Encapsulation"; Langmuir; 20; pp. 3398-3406; (2004).

Calva-Calle et al.; "A Linear Peptide Containing Minimal T- and B-Cell Epitopes of Plasmodium falciparum Circumsporozoite Protein Elicits Protection against Transgenic Sporozoite Challenge"; Infection and Immunity; pp. 6929-6939; (2006).

Chong et al.; "A Paradigm for Peptide Vaccine Delivery Using Viral Epitopes Encapsulated in Degradable Polymer Hydrogel Capsules"; Biomaterials; 30; pp. 5178-5186; (2009).

Cyr et al.; "C57B1/6 Mice are Protected From Respiratory Syncytial Virus (RSV) Challenge and IL-5 Associated Pulmonary Eosinophilic Infiltrates Following Intranasal Immunization with Protollin-eRSV Vaccine"; Vaccine 25; pp. 3228-3232; (2007).

Cyr et al.; "Intranasal Proteosome-based Respiratory Syncytial Virum (RSV) Vaccines Protect BALB/c Mice Against Challenge Without Eosinophilia or Enhanced Pathology"; Vaccine; 25; pp. 5378-5389; (2007).

De Haes et al.; "Polyelectrolyte Capsules-Containing HIV-1 p24 and Poly I:C Modulate Dendritic Cells to Stimulate HIV-1-specific Immune Responses"; Molecular Therapy 18(7); pp. 1408-1416; (2010).

Demento et al.; "Inflammasome-Activating Nanoparticles as Modular Systems for Optimizing Vaccine Efficacy"; Vaccine; 27; pp. 3013-3021; (2009).

DeMuth et al.; "Releasable Layer-by-Layer Assembly of Stabilized Lipid Nanocapsules on Microneedles for Enhanced Transcutaneous Vaccine Delivery"; ACS NANO; 6(9); pp. 8041-8051; (2012).

Hancock et al.; "Adjuvants Recognized by Toll-like Receptors Inhibit the Induction of Polarized Type 2 T Cell Responses by Natural Attachment (G) Protein of Respiratory Syncytial Virus"; Vaccine; 21; pp. 4348-4358; (2003).

Hill et al.; "Vaccines Against Malaria"; Phil. Trans. R. Soc. B.; 366; pp. 2806-2814; (2011).

Kumar et al.; "Quantitative Plasmodium Sporozoite Neutralization Assay (TSNA)" Journal of Immunological Methods; 292; pp. 157-164; (2004).

Moon et al.; "Antigen-Displaying Lipid-Enveloped PLGA Nanoparticles as Delivery Agents for a Plasmodium vivax Malaria Vaccine"; PLOS ONE; 7(2); pp. 1-17; (2012).

Moreno et al.; "CD4+ Cell Clones Obtained from Plasmodium falciparum Sporozoite-Immunized Volunteers Recognize Polymorphic Sequences of the Circumsporozoite Protein"; The Journal of Immunology; 151; pp. 489-499; (1993).

(Continued)

*Primary Examiner* — Julie Ha

(74) *Attorney, Agent, or Firm* — Cantor Colburn LLP

(57) ABSTRACT

Described herein are multilayer films that include modified polypeptide epitopes from *Plasmodium falciparum*, specifically a modified T* epitope. The multilayer films are capable of eliciting an immune response in a host upon administration to the host. The multilayer films can include at least one designed peptide that includes the modified T* polypeptide epitope from a *Plasmodium* protozoan.

13 Claims, 10 Drawing Sheets

(56) References Cited

OTHER PUBLICATIONS

Nardin et al.; "A Totally Synthetic Polyoxime Malaria Vaccine Containing Plasmodium Falciparum B Cell and Universal T Cell Epitopes Elicits Immune Responses in Volunteers of Diverse HLA Types"; The Journal of Immunology, The American Association of Immunologists, 166(1), pp. 481-489 (2001).

Su et al.; "Layer-by-Layer-Assembled Multilayer Films for Transcutaneous Drug and Vaccine Delivery"; ACS NANO; 3(11); pp. 3719-3729; (2009).

Nardin et al.; "Conserved Repetitive Epitope Recognized by CD4+ Clones from a Malaria-Immunized Volunteer"; Reports; 246; pp. 1603-1606; (2009).

Persson et al.; "Culling Edge: A New Tool to Evaluate Human Pre-Erythrocytic Malaria Vaccines: Rodent Parasites Bearing a Hybrid Plasmodium falciparum Circumsporozoite Protein"; The Journal of Immunology; 169; pp. 6681-6685; (2002).

Phelps et al.; "Nanofilm Biomaterials: Localized Cross-Linking to Optimize Mechanical Rigidity and Bioactivity"; Langmuir 27(3); pp. 1123-1130; (2011).

Powell et al., "Plasmodium Falciparum Synthetic LbL Microparticle Vaccine Elicits Protective Neutralizing Antibody and Parasite-Specific Cellular Immune Responses"; Vaccine; 31; pp. 1898-1904; (2013).

Powell et al.; "Synthetic Nanoparticles Vaccines Produced by Layer-by-Layer Assembly of Artificial Biofilms Induce Potent Protective T-cell and Antibody Responses in vivo"; Vaccine; 29; pp. 558-569; (2011).

Stanisic et al.; "Escaping the Immune System: How the Malaria Parasite Makes Vaccine Development a Challenge"; Trends in Parasitology; 29(12); pp. 612-622; (2013).

* cited by examiner

ANTI-MALARIA COMPOSITIONS AND METHODS

CROSS-REFERENCE TO RELATED APPLICATIONS

This application claims priority to U.S. Provisional Application 62/219,260 filed on Sep. 16, 2015, which is incorporated herein by reference in its entirety.

STATEMENT REGARDING FEDERALLY SPONSORED RESEARCH & DEVELOPMENT

This invention was made with government support under AI091089 awarded by the National Institutes of Health. The government has certain rights in the invention.

FIELD OF THE DISCLOSURE

The present disclosure relates to compositions and methods for the prevention of malaria infections, specifically multilayer film compositions containing antigenic epitopes.

BACKGROUND

Malaria is one of the most prevalent infections in tropical and subtropical areas throughout the world. Malaria infections lead to severe illnesses in hundreds of millions of individuals worldwide, leading to death in millions of individuals, primarily in developing and emerging countries every year. The widespread occurrence and elevated incidence of malaria are a consequence of the increasing numbers of drug-resistant parasites and insecticide-resistant parasite vectors. Other factors include environmental and climatic changes, civil disturbances, and increased mobility of populations.

Malaria is caused by the mosquito-borne hematoprotozoan parasites belonging to the genus *Plasmodium*. Four species of *Plasmodium* protozoa (*P. falciparum, P. vivax, P. ovale* and *P. malariae*) are responsible for the disease in man; many others cause disease in animals, such as *P. yoelii* and *P. berghei* in mice. *P. falciparum* accounts for the majority of human infections and is the most lethal type, sometimes called "tropical malaria". Malaria parasites have a life cycle consisting of several stages. Each stage is able to induce specific immune responses directed against the corresponding occurring stage-specific antigens. A current area of focus is development of vaccines that elicit immunity against the sporozoite stage pathogen. The sporozoite grows in the saliva of infected mosquitoes and is transferred to the human during the mosquito bite. The sporozoite travels thorough the blood stream to the liver where it enters hepatocytes and multiplies. Sporozoites are covered with many copies of the circumsporozoite coat protein (CS). Antibodies that bind to CS proteins can neutralize the organism and prevent liver invasion, so agents that elicit potent and long lasting anti-CS responses are expected to be useful malaria vaccines.

Currently there are two vaccines in clinical trials that seek to prevent malaria infections via the CS neutralization mechanism. RTS,S is a virus like particle vaccine that presents multiple copies of CS on a virus-like particle. It has been shown to protect both adults and children from infection but since efficacy is less than 50% its utility is still a matter for debate. Sanaria Inc. has proposed the use of killed sporozoites as an effective vaccine but the method of production involves the dissection of host mosquito saliva glands, a process that is tedious and may not be scalable to practical quantities. Hence there is a need for improved antigenic compositions that elicit immune responses which recognize and neutralize the malaria organism.

SUMMARY

In one aspect, an isolated peptide comprises the sequence of SEQ ID NO: 5.

In another aspect, a composition comprises a first multilayer film comprising a plurality of oppositely charged polyelectrolyte layers, wherein one of the polyelectrolyte layers in the multilayer film comprises a first antigenic polyelectrolyte, wherein the first antigenic polyelectrolyte comprises a modified *Plasmodium falciparum* circumsporozoite T* epitope of SEQ ID NO: 5, and wherein the polyelectrolytes in the multilayer film comprise a polycationic material or a polyanionic material having a molecular weight of greater than 1,000 and at least 5 charges per molecule.

In another embodiment, a method of eliciting an immune response in a vertebrate organism comprising administering into the vertebrate organism the multilayer film composition described above.

Figure 1:
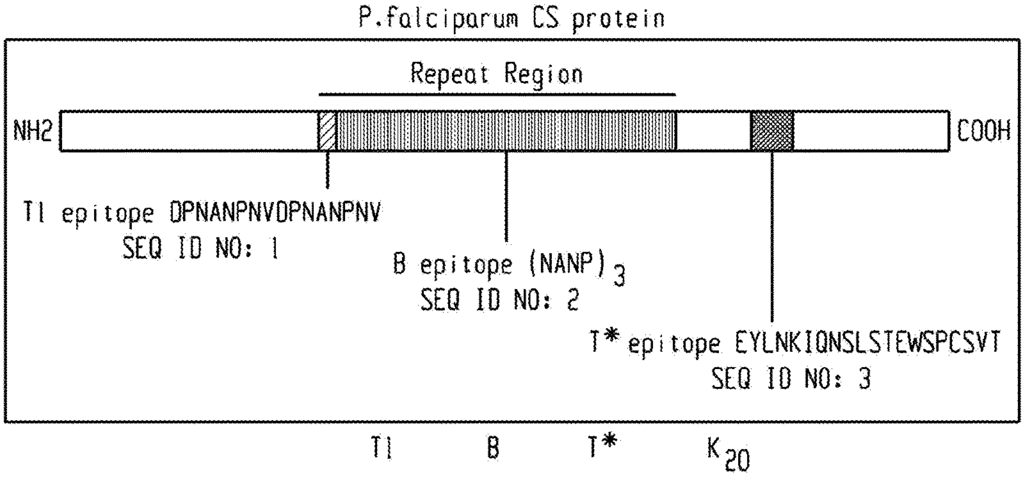
FIG. 1 shows the epitopes of *P. falciparum* CS protein showing the locations and sequences of the T1, B, and T* epitopes.

The above-described and other features will be appreciated and understood by those skilled in the art from the following detailed description, drawings, and appended claims.

DETAILED DESCRIPTION

Disclosed herein are multilayer films comprising modified polypeptide epitopes from a *Plasmodium* protozoan, wherein the multilayer films are capable of eliciting an immune response in a host upon administration to the host. Specifically, the films comprise one or more *Plasmodium falciparum* circumsporozoite protein antigens, wherein the circumsporozoite protein antigens include a modified T* epitope or a modified T1BT* epitope.

As used herein, the *Plasmodium falciparum* circumsporozoite protein antigens are:

```
T1:
                                        (SEQ ID NO: 1)
DPNANPNVDPNANPNV

B:
                                        (SEQ ID NO: 2)
NANPNANPNANP

T*:
                                        (SEQ ID NO: 3)
EYLNKIQNSLSTEWSPCSVT

T1BT*:
                                        (SEQ ID NO: 4)
DPNANPNVDPNANPNVNANPNANPNANPEYLNKIQNSLS
TEWSPCSVT
```

In one aspect, a modified T* epitope is:

```
                                        (SEQ ID NO: 5)
      EYLNKIQNSLSTEWSPSSVT,
      or
                                        (SEQ ID NO: 6)
      EYLNKIQNSLSTEWSPASVT.
```

In a related aspect, a modified T1BT* epitope is:

```
                                            (SEQ ID NO: 7)
DPNANPNVDPNANPNVNANPNANPNANPEYLNKIQNSLSTEWSPSSV
T,

or
                                            (SEQ ID NO: 8)
DPNANPNVDPNANPNVNANPNANPNANPEYLNKIQNSLSTEWSPASV
T.
```

During production of designed peptides for inclusion in multilayer films, there was a concern that interchain disulfide bonds might be formed during peptide synthesis or film production. The modified T* epitopes of SEQ ID Nos. 5 and 6 were designed to modify the unpaired Cys residue in the wild-type T* epitope to provide a significant advantage during the manufacturing process of designed peptides and multilayer films. When microparticles containing designed T1BT* peptides with the modified T* epitopes of SEQ ID Nos. 5 and 6 were tested in an animal model, it was found that while peptides containing SEQ ID NO: 5 elicited a T-cell response specific for the wild-type T1B peptide (SEQ ID NO: 4), peptides containing SEQ ID NO: 6 failed to elicit a T-cell response specific for the wild-type T1B peptide. It was completely unexpected that the substitution of a Ser residue would be tolerated, while an Ala substitution would not be tolerated.

Specifically, multilayer films comprise alternating layers of oppositely charged polyelectrolytes, wherein one of the layers comprises a modified T* peptide, or a T1BT* peptide containing a modified T* epitope, specifically SEQ ID NO: 5 (modified T* epitope) or SEQ ID NO: 7 (modified T1BT* epitope). Optionally, one or more of the polyelectrolytes, specifically a polyelectrolyte comprising the modified T* or modified T1BT* peptide is a polypeptide. In certain embodiments, the multilayer films comprise multiple epitopes from a *Plasmodium* protozoan. For example, first and second *Plasmodium* protozoan polypeptide epitopes can be attached to the same or different polyelectrolytes, and/or can be present in the same or different multilayer film.

In one aspect, the modified T* peptide, or a T1BT* peptide containing a modified T* epitope, is covalently linked to a polycationic material or a polyanionic material having a molecular weight of greater than 1,000 and at least 5 charges per molecule. The polycationic or polyanionic material provides sufficient charge for deposition of the modified T* peptide or T1BT* peptide containing a modified T* epitope into a layer of a multilayer film.

In another aspect, the modified T* peptide or T1BT* peptide containing a modified T* epitope is covalently linked to one or two surface adsorption regions at the C-terminus and/or the N-terminus of the polypeptide, wherein at least one of the surface adsorption regions comprises five or more, such as 10 to 20, negatively or positively charged amino acid residues. The surface adsorption regions provide sufficient charge for deposition of the modified T* peptide or T1BT* peptide containing a modified T* epitope into a layer of a multilayer film. In one embodiment, the net charge per residue of the antigenic polypeptide (including the T* epitope and the surface adsorption regions) is greater than or equal to 0.1, 0.2, 0.3, 0.4, or 0.5 at pH 7.0.

In one embodiment, a composition comprises a first multilayer film comprising a plurality of oppositely charged polyelectrolyte layers, wherein one of the polyelectrolyte layers in the multilayer film comprises a first antigenic polyelectrolyte, wherein the first antigenic polyelectrolyte comprises a modified *Plasmodium falciparum* circumsporozoite T* epitope, and wherein the polyelectrolytes in the multilayer film comprise a polycationic material or a polyanionic material having a molecular weight of greater than 1,000 and at least 5 charges per molecule. In another embodiment, a composition comprises a first multilayer film comprising a plurality of oppositely charged polyelectrolyte layers, wherein one of the polyelectrolyte layers in the multilayer film comprises a first antigenic polyelectrolyte, wherein the first antigenic polyelectrolyte comprises a modified *Plasmodium falciparum* circumsporozoite T1BT* epitope, and wherein the polyelectrolytes in the multilayer film comprise a polycationic material or a polyanionic material having a molecular weight of greater than 1,000 and at least 5 charges per molecule. In one aspect, the modified T* epitope has SEQ ID NO: 5. In another aspect, the modified T1BT* epitope has SEQ ID NO: 7.

In one embodiment, the first antigenic polyelectrolyte comprises two of the *Plasmodium falciparum* circumsporozoite epitopes, such as T1T*, BT*, in any order, wherein the T* epitope is a modified T* epitope. The epitopes can be contiguous on the polypeptide chain, or spaced by a spacer region. Similarly, the epitopes can be at the N-terminus of the polypeptide, the C-terminus of the polypeptide, or anywhere in between. In yet another embodiment, the first polyelectrolyte is a polypeptide comprising all three of the *Plasmodium falciparum* circumsporozoite T1, B, and modified T* epitopes. The T1, B, and modified T* epitopes can be in a contiguous part of the polypeptide, or any or all of the epitopes can be separated by a spacer region.

In one aspect, the modified T* peptide, or a T1BT* peptide containing a modified T* epitope, in the multilayer film is covalently linked to a polycationic material or a polyanionic material having a molecular weight of greater than 1,000 and at least 5 charges per molecule. The polycationic or polyanionic material provides sufficient charge for deposition of the modified T* peptide or T1BT* peptide containing a modified T* epitope into a layer of a multilayer film.

In one aspect, in order to facilitate deposition of the modified T* or modified T1BT* epitope into a multilayer film, the peptide comprises one or more highly charged surface adsorption regions, such as at the N-terminus, the C-terminus, or both. In one aspect, at least one of the surface adsorption regions comprises five or more negatively or positively charged amino acid residues. Peptides containing an antigenic peptide and one or more surface adsorption regions are denoted herein as designed polypeptides (DP).

It is noted that when the first antigenic polyelectrolye is a polypeptide, the polypeptide contains sufficient charge for deposition into a polypeptide multilayer film. In one embodiment, the net charge per residue of the polypeptide is greater than or equal to 0.1, 0.2, 0.3, 0.4 or 0.5 at pH 7.0, as explained herein.

In another embodiment, instead of the *Plasmodium falciparum* circumsporozoite T1, B and modified T* epitopes being on the same polyelectrolyte, two or three epitopes can be presented on separate polyelectrolytes, and layered into the same multilayer film. In one embodiment, the first multilayer film further comprises a second antigenic polyelectrolyte comprising a *Plasmodium falciparum* circumsporozoite T1, B, or modified T* epitope covalently linked to a second polyelectrolyte, wherein the first and second antigenic polyelectrolytes comprise different *Plasmodium falciparum* circumsporozoite epitopes. In a further embodiment, the first multilayer film further comprises a third antigenic polyelectrolyte comprising a *Plasmodium falciparum* circumsporozoite T1, B, or modified T* epitope covalently linked to a third polyelectrolyte, wherein the first, second and third antigenic polyelectrolytes comprise different *Plasmodium falciparum* circumsporozoite epitopes. In one embodiment, the first, second and/or third polyelectrolyte is a polypeptide.

In one embodiment, a first, second and optionally third polyelectrolyte is presented in a separate multilayer film, such as two or three individual populations of coated cores, each population comprising a different multilayer film. Thus, in one embodiment, a composition comprises a first multilayer film as described above and a second multilayer film comprising a plurality of oppositely charged polyelectrolyte layers, wherein one of the layers in the second multilayer film comprises a second antigenic polyelectrolyte, wherein the second antigenic polyelectrolyte comprises a *Plasmodium falciparum* circumsporozoite T1, B or modified T* epitope covalently linked to a second polyelectrolyte, wherein the first and second antigenic polyelectrolytes comprise different *Plasmodium falciparum* circumsporozoite epitopes. In a further embodiment, the composition further comprises a third multilayer film comprising a plurality of oppositely charged polyelectrolyte layers, wherein one of the layers in the third multilayer film comprises a third antigenic polyelectrolyte, wherein the third antigenic polyelectrolyte comprises a *Plasmodium falciparum* circumsporozoite T1, B, or modified T* epitope covalently linked to a third polyelectrolyte, wherein the first, second and third antigenic polyelectrolytes comprise different *Plasmodium falciparum* circumsporozoite epitopes. In certain embodiments, the first, second and or third polyelectrolyte is a polypeptide. In some embodiments, the first, second and third multilayer films are layered onto separate core particles, such that a composition comprises two or three distinct populations of particles.

In certain embodiments, the multilayer films further comprise a toll-like receptor ligand. As used herein, toll-like receptor ligands, or TLR ligands, are molecules that bind to TLRs and either activate or repress TLR receptors. Activation of TLR signaling through recognition of pathogen-associated molecular patterns (PAMPs) and mimics leads to the transcriptional activation of genes encoding pro-inflammatory cytokines, chemokines and co-stimulatory molecules, which can control the activation of the antigen-specific adaptive immune response. TLRs have been pursued as potential therapeutic targets for various inflammatory diseases and cancer. Following activation, TLRs induce the expression of a number of protein families, including inflammatory cytokines, type I interferons, and chemokines. TLR receptor ligands can function as adjuvants for the immune response.

Exemplary TLR ligands include a TLR1 ligand, a TLR2 ligand, a TLR3 ligand, a TLR4 ligand, a TLR5 ligand, a TLR6 ligand, a TLR 7 ligand, a TLR8 ligand, a TLR9 ligand and combinations thereof.

Exemplary TLR1 ligands include bacterial lipopeptides. Exemplary TLR2 ligands include lipopeptides such as Pam3Cys ([N-palmitoyl-S-[2,3-bis(palmitoyloxy)propyl] cysteine]) and Pam2Cys ([S-[2,3-bis(palmitoyloxy)propyl] cysteine]). Exemplary TLR6 ligands are diacyl lipopeptides. TLR1 and TLR6 require heterodimerization with TLR2 to recognize ligands. TLR1/2 are activated by triacyl lipoprotein (or a lipopeptide, such as a Pam3Cys peptide), whereas TLR6/2 are activated by diacyl lipoproteins (e g., Pam2Cys), although there may be some cross-recognition.

An exemplary TLR3 ligand is Poly(I:C). Exemplary TLR4 ligands are lipopolysaccharide (LPS) and monophospholipid A (MPLA). An exemplary TLR5 ligand is flagellin. An exemplary TLR7 ligand is imiquimod. An exemplary TLR8 ligand is single-stranded RNA. An exemplary TLR9 ligand is unmethylated CpG Oligodeoxynucleotide DNA.

In one embodiment, the first, second, or third antigenic polyelectrolyte, e.g., an antigenic polypeptide, has a TLR ligand covalently attached thereto. For example, Pam3Cys can be covalently coupled to a polypeptide chain by standard polypeptide synthesis chemistry.

In another embodiment, a substrate such as a template core has deposited thereon a TLR ligand prior to deposition of polyelectrolyte layers. In another embodiment, a TLR ligand is co-deposited with one or more polyelectrolyte layers during assembly of the multilayer film.

In one embodiment, the multilayer film is deposited on a core particle, such as a core nanoparticle or a core microparticle. Exemplary cores include $CaCO_3$ nanoparticles and microparticles, latex particles, and iron particles. Particle sizes on the order of 5 nanometers (nm) to 500 micrometers (μm) in diameter are useful. Particles having diameters of 0.05-20 μm are preferred for vaccine purposes. Particles of approximate diameter 1-10 μm are particularly useful as vaccines Particles made of other materials can also be used as cores provided that they are biocompatible, have controllable size distribution, and have sufficient surface charge (either positive or negative) to bind polyelectrolyte peptides. Examples include nanoparticles and microparticles made of materials such as polylactic acid (PLA), polylactic acid glycolic acid copolymer (PLGA), polyethylene glycol (PEG), chitosan, hyaluronic acid, gelatin, or combinations thereof. Core particles could also be made of materials that are believed to be inappropriate for human use provided that they can be dissolved and separated from the multilayer film following film fabrication. Examples of the template core substances include organic polymers such as latex or inorganic materials such as silica.

Polyelectrolyte multilayer films are thin films (e.g., a few nanometers to micrometers thick) composed of alternating layers of oppositely charged polyelectrolytes. Such films can be formed by layer-by-layer assembly on a suitable substrate. In electrostatic layer-by-layer self-assembly ("LBL"), the physical basis of association of polyelectrolytes is electrostatic attraction. Film buildup is possible because the sign of the surface charge density of the film reverses on deposition of successive layers. The generality and relative simplicity of the LBL film process permits the deposition of many different types of polyelectrolyte onto many different types of surface. Polypeptide multilayer films are a subset of polyelectrolyte multilayer films, comprising at least one layer comprising a charged polypeptide, herein referred to as a designed polypeptide (DP). A key advantage of polypeptide multilayer films over films made from other polymers is their biocompatibility.

LBL films can also be used for encapsulation of other materials. Applications of polypeptide films and microcapsules include, for example, nano-reactors, biosensors, artificial cells, and drug delivery vehicles.

The term "polyelectrolyte" includes polycationic and polyanionic materials having a molecular weight of greater than 1,000 and at least 5 charges per molecule. Suitable polycationic materials include, for example, polypeptides and polyamines. Polyamines include, for example, a polypeptide such as poly-L-lysine (PLL) or poly-L-ornithine, polyvinyl amine, poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), poly (diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide such as poly-L-glutamic acid (PGA) and poly-L-aspartic acid, a nucleic acid oligomer such as DNA and RNA, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials. In one embodiment, the *Plasmodium* protozoan epitope and the polyelectrolyte have the same sign of charge. In another embodiment, the *Plasmodium* protozoan epitope and the polyelectrolyte have the opposite sign of charge.

In one embodiment, one or more polyelectrolyte layers of the film, optionally including the polyelectrolyte comprising the *Plasmodium* protozoan epitope, is a designed polypeptide. In one embodiment, the design principles for polypeptides suitable for electrostatic layer-by-layer deposition are elucidated in U.S. Patent Publication No. 2005/0069950, incorporated herein by reference for its teaching of polypeptide multilayer films. Briefly, the primary design concerns are the length and charge of the polypeptide. Electrostatics is the most important design concern because it is the basis of LBL. Without suitable charge properties, a polypeptide may not be substantially soluble in aqueous solution at pH 4 to 10 and cannot readily be used for the fabrication of a multilayer film by LBL. Other design concerns include the physical structure of the polypeptides, the physical stability of the films formed from the polypeptides, and the biocompatibility and bioactivity of the films and the constituent polypeptides.

A designed polypeptide means a polypeptide that has sufficient charge for stable binding to an oppositely charged surface, that is, a polypeptide that can be deposited into a layer of a multilayer film wherein the driving force for film formation is electrostatic attraction. A short stable film is a film that once formed, retains more than half its components after incubation in PBS at 37° C. for 24 hours. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. Positively-charged (basic) naturally-occurring amino acids at pH 7.0 are arginine (Arg), histidine (His), ornithine (Orn), and lysine (Lys). Negatively-charged (acidic) naturally-occurring amino acid residues at pH 7.0 are glutamic acid (Glu) and aspartic acid (Asp). A mixture of amino acid residues of opposite charge can be employed so long as the overall net ratio of charge meets the specified criteria. In one embodiment, a designed polypeptide is not a homopolymer. In another embodiment, a designed polypeptide is unbranched.

The electrostatic attraction between oppositely charged polyelectrolytes is usually sufficient to produce a film that is stable under ambient conditions, for example at neutral pH and body temperature. However, film stability can be increased by engineering covalent bonds between the layers after the film is formed. This cross-linking process confers additional stability upon the film and can enable it to withstand more stringent conditions such higher temperatures or large changes in pH. Examples of covalent bonds useful for cross-linking include disulfides bonds, thioether bonds, amide bonds, and others. For films comprised of polypeptides, chemistries that produce amide bonds are particularly useful. In the presence of appropriate coupling reagents, acidic amino acids (those with side chains containing carboxylic acid groups such as aspartic acid and glutamic acid) will react with amino acids whose side chains contain amine groups (such as lysine and ornithine) to form amide bonds. Amide bonds are more stable than disulfide bonds under biological conditions and amide bonds will not undergo exchange reactions. Many reagents can be used to activate polypeptide side chains for amide bonding. Carbodiimide reagents, such as the water soluble 1-ethyl-3-(3-dimethylaminopropyl) carbodiimide (EDC) will react with aspartic acid or glutamic acid at slightly acidic pH, forming an intermediate product that will react irreversibly with an amine to produce an amide bond. Additives such as N-hydroxysuccinimide (NHS) are often added to the reaction to accelerate the rate and efficiency of amide formation. After cross-linking the soluble reagents and byproducts are removed from the nanoparticles or microparticles by, for example, centrifugation and aspiration. Alternatively, soluble reagents can be removed by filtration of the particles, for example, by tangential flow filtration (TFF). Examples of other coupling reagents include diisopropylcarbodiimide, HBTU, HATU, HCTU, TBTU, and PyBOP. Examples of other additives include sulfo-N-hydroxysuccinimide (sulfo-NHS), 1-hydroxbenzotriazole, and 1-hydroxy-7-aza-benzotriazole. The extent of amide cross-linking can be controlled by modulating the stoichiometry of the coupling reagents, the time of reaction, or the temperature of the reaction, and can be monitored by techniques such as Fourier transform-infrared spectroscopy (FT-IR).

Covalently cross-linked LBL films have desirable properties such as increased stability. Greater stability allows for more stringent conditions to be used during nanoparticle, microparticle, nanocapsule, or microcapsule fabrication. Examples of stringent conditions include high temperatures, low temperatures, cryogenic temperatures, high centrifugation speeds, high salt buffers, high pH buffers, low pH buffers, filtration, and long term storage. In one aspect, at least two polyelectrolyte layers of the multilayer film, other than the layer containing the first antigenic polyelectrolyte, are covalently cross-linked. The covalent cross-link bonds are, for example, amide bonds involving amino acid side chain functional groups.

A method of making a polyelectrolyte multilayer film comprises depositing a plurality of layers of oppositely charged chemical species on a substrate. In one embodiment, at least one layer comprises a designed polypeptide. Successively deposited polyelectrolytes will have opposite net charges. In one embodiment, deposition of a polyelectrolyte comprises exposing the substrate to an aqueous solution comprising a polyelectrolyte at a pH at which it has a suitable net charge for LBL. In other embodiments, the deposition of a polyelectrolyte on the substrate is achieved by sequential spraying of solutions of oppositely charged polypeptides. In yet other embodiments, deposition on the substrate is by simultaneous spraying of solutions of oppositely charged polyelectrolytes.

In the LBL method of forming a multilayer film, the opposing charges of the adjacent layers provide the driving force for assembly. It is not critical that polyelectrolytes in opposing layers have the same net linear charge density, only that opposing layers have opposite net charges. One standard film assembly procedure by deposition includes forming aqueous solutions of the polyelectrolytes at a pH at which they are ionized (i.e., pH 4-10), providing a substrate bearing a surface charge, and alternating immersion of the substrate into the charged polyelectrolyte solutions. The substrate is optionally washed in between deposition of alternating layers to remove unbound polyelectrolyte.

The concentration of polyelectrolyte suitable for deposition of the polyelectrolyte can readily be determined by one of ordinary skill in the art. An exemplary concentration is 0.1 to 10 mg/mL.

In addition, the number of layers required to form a stable polyelectrolyte multilayer film will depend on the polyelectrolytes in the film. For films comprising only low molecular weight polypeptide layers, a film will typically have two or more bilayers of oppositely charged polypeptides. Studies have shown that polyelectrolyte films are dynamic. The polyelectrolytes contained within a film can migrate between layers and can exchange with soluble polyelectrolytes of like charge when suspended in a polyelectrolyte solution. Moreover polyelectrolyte films can disassemble or dissolve in response to a change in environment such as temperature, pH, ionic strength, or oxidation potential of the suspension buffer. Thus some polyelectrolytes and particularly peptide polyelectrolytes exhibit transient stability. The stability of peptide polyelectrolyte films can be monitored by suspending the films in a suitable buffer under controlled conditions for a fixed period of time, and then measuring the amounts of the peptides within the film with a suitable assay such as amino acid analysis, HPLC assay, or fluorescence assay. Peptide polyelectrolyte films are most stable under conditions that are relevant to their storage and usage as vaccines, for example in neutral buffers and at ambient temperatures such as 4° C. to 37° C. Under these conditions stable peptide polyelectrolyte films will retain most of their component peptides for at least 24 hours and often up to 14 days and beyond.

In one embodiment, a designed polypeptide comprises one or more surface adsorption regions covalently linked to one or more *Plasmodium* protozoan epitopes. As used herein, a surface adsorption region is a charged region of a designed polypeptide that advantageously provides sufficient charge so that a peptide containing an epitope from a *Plasmodium* protozoan, for example, can be deposited into a multilayer film. The one or more surface adsorption regions and the one or more *Plasmodium* protozoan epitopes can have the same or opposite polarity. In another embodiment, the solubility of the designed polypeptide at pH 4 to 10 is greater than or equal to about 0.1 mg/mL. In another embodiment, the solubility of the designed polypeptide at pH 4 to 10 is greater than or equal to about 1 mg/mL. The solubility is a practical limitation to facilitate deposition of the polypeptides from aqueous solution.

An exemplary surface adsorption region comprises 20 consecutive lysine residues ($K_{20}$ or $K_{20}Y$). When the *Plasmodium* protozoan epitope is the modified T1BT* epitope of SEQ ID NO: 7, for example, it is preferred that the surface adsorption region(s) include 5 to 20 positively charged amino acid residues, or 5 to 20 negatively charged amino acid residues.

In one embodiment, a designed polypeptide comprises a single antigenic *Plasmodium* protozoan epitope flanked by two surface adsorption regions, an N-terminal surface adsorption region and a C-terminal surface adsorption region. In another embodiment, a designed polypeptide comprises a single antigenic *Plasmodium* protozoan epitope flanked by one surface adsorption region linked to the N-terminus of the *Plasmodium* protozoan epitope. In another embodiment, a designed polypeptide comprises a single antigenic *Plasmodium* protozoan epitope flanked by one surface adsorption region linked to the C-terminus of the *Plasmodium* protozoan epitope.

Each of the independent regions (e.g., *Plasmodium* protozoan epitopes and surface adsorption regions) of the designed polypeptide can be synthesized separately by solution phase peptide synthesis, solid phase peptide synthesis, or genetic engineering of a suitable host organism. A combination of solution phase and solid phase methods can be used to synthesize relatively long peptides and even small proteins. Peptide synthesis companies have the expertise and experience to synthesize difficult peptides on a fee-forservice basis. The syntheses are performed under good manufacturing practices (GMP) condition and at scales suitable for clinical trials and commercial drug launch.

Alternatively, the various independent regions can be synthesized together as a single polypeptide chain by solution-phase peptide synthesis, solid phase peptide synthesis or genetic engineering of a suitable host organism. The choice of approach in any particular case will be a matter of convenience or economics.

If the various *Plasmodium* protozoan epitopes and surface adsorption regions are synthesized separately, once purified, for example, by ion exchange chromatography or by high performance liquid chromatography, they can be joined by peptide bond synthesis. That is, the N-terminus of the surface adsorption region and the C-terminus of one or more of the *Plasmodium* protozoan epitopes are covalently joined to produce the designed polypeptide. Alternatively, the C-terminus of the surface adsorption region and the N-terminus of the *Plasmodium* protozoan epitope are covalently joined to produce the designed polypeptide. The individual fragments can be synthesized by solid phase methods and obtained as fully protected, fully unprotected, or partially protected segments. The segments can be covalently joined in a solution phase reaction or solid phase reaction. If one polypeptide fragment contains a cysteine as its N-terminal residue and the other polypeptide fragment contains a thioester or a thioester precursor at its C-terminal residue the two fragments will couple spontaneously in solution by a specific reaction commonly known to those skilled in the art as native cysteine ligation. Native cysteine ligation is a particularly attractive option for designed peptide synthesis because it can be performed with fully deprotected or partially protected peptide fragments in aqueous solution and at dilute concentrations.

In one embodiment, the *Plasmodium* protozoan epitopes and/or surface adsorption regions are joined by peptidic or non-peptidic linkages as described in U.S. Pat. No. 7,723,294, incorporated herein by reference for its teaching of the use of non-peptidic linkages to join segments of polypeptides for use in multilayer films. Suitable non-peptidic linkers include, for example, alkyl linkers such as $—NH—(CH_2)_s—C(O)—$, wherein s=2-20. Alkyl linkers are optionally substituted by a non-sterically hindering group such as lower alkyl (e.g., $C_1$-$C_6$), lower acyl, halogen (e.g., Cl, Br), CN, $NH_2$, phenyl, and the like. Another exemplary non-peptidic linker is a polyethylene glycol linker such as $—NH—(CH_2—CH_2—O)_n,—C(O)—$ wherein n is such that the linker has a molecular weight of about 100 to about 5000 Da. Many of the linkers described herein are available from commercial vendors in a form suitable for use in solid phase peptide synthesis.

In one embodiment, one or more of the polypeptide epitopes from a *Plasmodium* protozoan is covalently attached to one or more of the polyelectrolyes, such as a polypeptide or other polyelectrolyte, through covalent bonds. Examples of suitable covalent bonds include amides, esters, ethers, thioethers, and disulfides. One skilled in the art can take advantage of a range of functional groups found within the epitope peptide to engineer a bond to a suitable electrolyte. For instance, a carboxylic acid in the epitope peptide can be found either at the C-terminal or on the side chain of amino acids aspartic acid or glutamic acid. Carboxylic acids can be activated with suitable peptide coupling reagents such as 1-ethyl-3-(3-dimethylaminopropyl) carbodiimide (EDC) for reaction with primary or secondary amines that are found in peptide polyelectrolytes such as poly-L-lysine. The resulting amide bond is stable under ambient conditions. Conversely, the acid groups in a peptide polyelectrolyte can be activated with EDC for reaction with amine groups in the epitope peptide. Useful amine groups can be found at the epitope peptide's N-terminal or on the side chain of lysine residues.

Epitope peptides can also be attached to polyelectrolytes via thioether bonds. Synthetic epitope peptides can be synthesized with appropriate electrophiles such as haloacetyl groups which react specifically with sulfhydryls. For instance, an epitope peptide containing a chloroacetyl at its N-terminal will form a stable bond to sulfhydryl bearing polyelectrolytes.

Epitope peptides can also be attached covalently to polyelectrolytes through bifunctional linker molecules. Bifunctional linkers usually contain two electrophilic groups that can react with nucleophiles present on either the epitope peptide or the polyelectrolyte molecule. Two classes of linker molecules are sold commercially, homobifunctional linkers and heterobifunctional linkers. Homobifunctional linkers contain two copies of an electrophilic group joined by a nonreactive spacer. Often the electophiles are active esters, such as N-hydroxysuccinimide (NHS) esters or sulfo-N-hyrdoxysuccinimide esters (sulfo-NHS) which react with nucleophilic amines. Examples of homobifunctional NHS esters include bis(sulfosuccinimidyl) suberate, disuccinimidyl glutarate, dithiobis(succinimidyl) propionate, disuccinimidyl suberate, disuccinimidyl tartrate. Sometimes the electophiles are aldehyde groups that form imides with nucleophilic amines on the epitope and polyelectrolyte molecules. The imide bonds are transiently stable but can be converted to stable structures with reducing agents such as sodium borohydride or catalytic hydrogenation. The most commonly used homobifunctional aldehyde linker is glutaraldehyde.

Other commonly used homobifunctional linkers contain electrophiles that react specifically with nucleophilic thiols, which can be used to link cysteine containing epitope peptides to sulfhydryl containing polyelectrolytes as described above. Examples of sulfhydryl specific homobifunctional linkers include 1,4-bismaleimidobutane, 1,4 bismaleimidyl-2,3-dihydroxybutane, vbismaleimidohexane, bis-maleimidoethane, 1,4-di-[3'-(2'-pyridyldithio)-propionamido]butane, dithio-bismaleimidoethane, 1,6-hexane-bis-vinylsulfone.

While designed polypeptides containing free cysteine residues are useful for covalent linking to other molecules, the free sulfhydral group can oxidize in a variety of ways that can be problematic. For example, two free cysteine containing peptides can undergo oxidative coupling and become covalently linked via a disulfide bond. When the free cysteine peptides are identical, the product is referred to a symmetrical disulfide or a disulfide dimer. Disulfide dimerization can occur under mild conditions, for example under ambient temperatures or even during cold storage. All that is required is brief exposure to a mild oxidant such as air oxygen or another mild oxidant. Moreover dimerization can occur when the free cysteine peptide is stored as a solid, for example as a dry powder, or in solution form, for example as a 1 mg/mL solution in water at neutral pH. In cases where the free cysteine peptides are prone to self-associate, essentially all of the monomeric free cysteine peptide can be converted to dimer. Even when careful steps are taken to exclude exposure to oxidants such as, for example, working in inert gas atmospheres or degassing of solvents and buffers, trace amounts or unwanted disulfide product can form.

Disulfide dimerization is a concern for vaccine compositions for a number of reasons. First, if a free cysteine peptide is part of a drug substance, the disulfide dimer would be considered an impurity and would require frequent monitoring, quantitation, and if present in sufficient amounts, removal and/or characterization for possible toxicities. Secondly, since disulfide dimers can accumulate over time, a free cysteine peptide drug substance is likely to have a shorter shelf life than peptides lacking free cysteines. Thirdly, if the cysteine is part of or near an important antibody or T-cell epitope, dimerization may obscure that epitope thus weakening the desired immune response. And finally, dimerization may create new antibody epitopes that are irrelevant to protection and thus dilute the desired immune response. Clearly, it is preferable to avoid using free cysteine peptides in drug substances unless the cysteine serves an important function, for example, if it is a critical component of an antibody or T-cell epitope, or will be used for conjugation or linking as described above.

In Example 5, a free cysteine containing T1BT*-K20 designed peptide (SEQ ID NO: 10) was subjected to various storage conditions and the purity of the peptide was monitored chromatographically. All storage conditions gave rise to new species that can be separated from the starting monomeric free cysteine peptide. This new peak is likely the result of cysteine oxidation, presumably to the symmetrical disulfide dimer, a conclusion that is supported by the observation that treatment with the reducing agent dithiothreitol (DTT) causes the new peak to revert back to the original free cysteine peptide. One would predict that this phenomenon likely would occur in all T1BT* peptides that contain a free cysteine. Thus there is a need to control or prevent this undesired side reaction from occurring.

Epitopes that elicit protective immune responses can be identified in a number of ways. Putative antibody epitopes can be identified by testing immune sera or monoclonal antibodies against subunits, deletion mutants, or point mutants of pathogen proteins in assays such as ELISA. Putative T-cell epitopes can be identified by testing immune peripheral blood mononuclear cells against overlapping peptides spanning the length of pathogen proteins in assays such as ELISPOT. In each case, the use of multiple overlapping and partially redundant subunit analytes allows one skilled in the art to identify the putative epitope that is recognized by the protective immune component, be it an antibody or a T-cell. The putative protective epitopes can then be validated by immunizing naïve animals with the defined epitope(s) and challenging with the pathogen of interest to determine whether the epitope-restricted immune response protects the host from infection or pathology.

After an antibody or T-cell epitope has been identified, it may be possible to substitute one or more of the individual amino acid residues without loss of function. Unfortunately it is difficult to predict which residues can be substituted, and which other residues can serve as suitable replacements. Thus new analogs with potentially allowed substitute residues must be prepared and tested in animal models or in surrogate in vitro assays that are predictive of the desired in vivo result. One can prepare a large number of peptide analogs using peptide array synthesis technologies but screening these in animal models may be time and cost prohibitive. Under such resource restrictions one can reduce the number of analogs to prepare and screen by limiting substitutions to those residues of similar size and/or functionality. Examples of amino acid residue pairs that have similar size and functionality, and are good candidates for substitution are: serine/threonine (Ser/Thr), isoleucine/valine (Ile/Val), phenylalanine/tyrosine (Phe/Tyr), isoleucine/leucine (Ile/Leu), asparagine/glutamine (Asn/Gln), asparagine/aspartic acid (Asn/Asp), glutamine/glutamic acid (Gln/Glu), aspartic acid/glutamic acid (Asp/Glu), and arginine/lysine (Arg/Lys). Glycine and proline are structurally distinct from the other natural amino acids so it would not be surprising to find no allowable substitutions for those residues.

By virtue of its high reactivity, hydrogen bonding properties, and tendency to oxidize, cysteine is unique amongst the natural amino acids. While cysteine contains the same number of heavy (non-hydrogen) atoms as serine, its side chain sulfhydral group is much more acidic than serine's hydroxyl group, and is partially ionized at neutral pH. Therefore, the best way to identify a substitute for a cysteine residue within a peptide epitope is it to make several sensible analogs and test those in a predictive assay, such as a mouse immunization model.

The T* epitope in the malaria CS protein has been found to be an important component of peptide based candidate malaria vaccines. It contains a cysteine residue (Cys334) that in the folded CS protein is disulfide bonded to a residue (Cys369) which lies outside of the T* region. As a T-cell epitope, immune compositions containing T* are taken up by antigen presenting cells, processed into shorter linear peptide segments, and bound to major histocompatibility complex (MHC) molecules in a linear conformation. The peptide:MHC complexes then translocate to the cell surface and present the peptide to T-cells that recognize the peptide: MHC complex via the T-cell receptor (TCR). In the case of the T* epitope, intracellular processing by the antigen presenting cell will reduce the native disulfide bond leaving Cys334 as a free cysteine. In theory it should be possible to replace Cys334 with another residue provided that interactions critical for MHC binding and recognition by T-cells are preserved.

Figure 5:
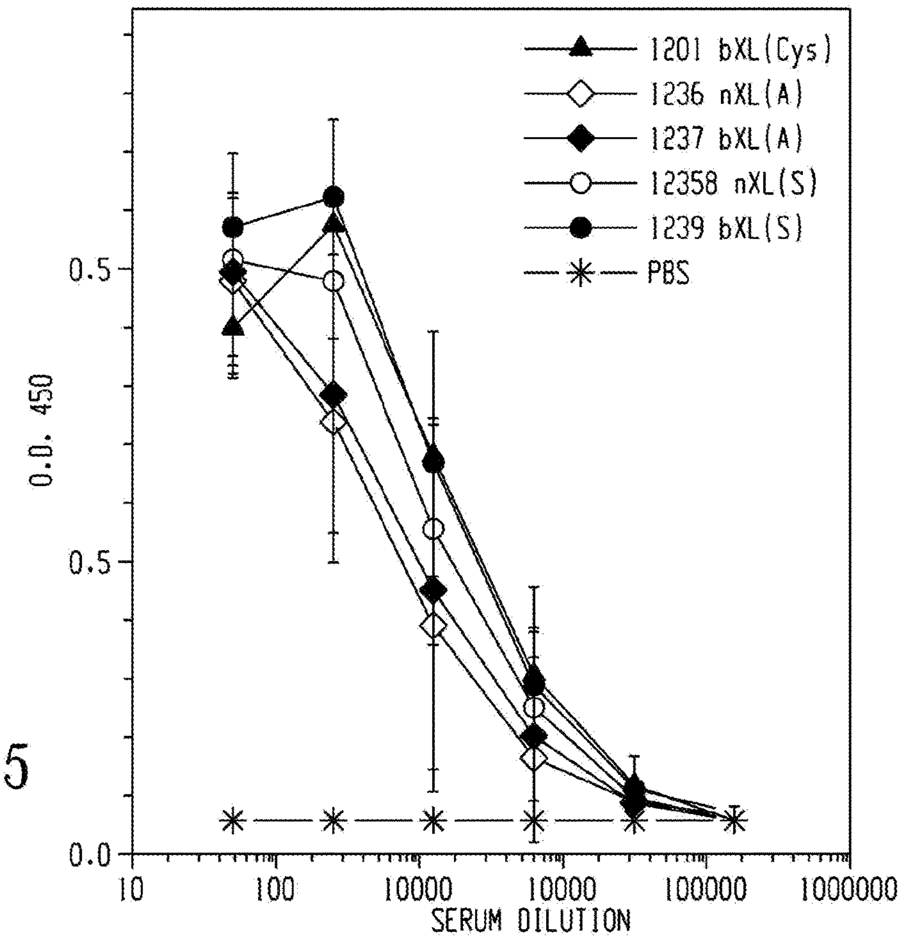
FIG. 5 shows the results for sera harvested on day 59 from C57BL/6J mice immunized with T1BT* microparticle constructs and tested in ELISA against T1B peptide.

The synthesis of designed peptides that contain T* cysteine substitutions is described in Example 1 and their fabrication into malaria vaccine microparticles is described in Example 2. Designed peptides Pam3Cys-T1BT*-K20 (Cys→Ser, SEQ ID NO: 13) and Pam3Cys-T1BT*-K20 (Cys→Ala, SEQ ID NO: 14) contain serine and alanine substitutions for Cys334, respectively. Microparticle vaccines containing these designed peptides as well as microparticles that contain the native free cysteine designed peptide Pam3Cys-T1BT*-K20 (SEQ ID NO: 11) were used to immunize mice as described in Example 3 and Example 4. Following immunizations the animals were challenged with mosquitos infected with a hybrid form of the mouse malaria organism *Plasmodium bergheii* (Pb) that has been genetically engineered to express the T1B repeat elements of the circumsporozoite (CS) coat protein from the human malaria organism *Plasmodium falciparum* (Pf). The PfPb transgenic organism enables vaccines targeted against the Pf CS protein to be tested in a challenge experiment in mice. In the experiment described in Example 3, all mouse cohorts responded to immunizations with strong anti-T1B polyclonal antibody responses (FIG. 5). This was the expected result as the various vaccine batches were similar in all respects except for base layer cross-linking and the residue at position 334 in the T* epitope. Closer inspection of the data reveals that the serine replacement (SEQ ID NO: 13) elicited mouse sera with anti-T1B titers equal to the cysteine containing sequence (SEQ ID NO: 11) while the alanine replacement (SEQ ID NO: 14) elicited lower titer anti-T1B sera. This result was unexpected as the substitution occurs in the T* region yet it appears to have an effect on antibody responses to the T1B epitopes. Thus, the T* epitope appears to affect the magnitude of the T1B specific antibody response, and non-optimal replacements for the native cysteine reduce the magnitude of the response.

Figure 6:
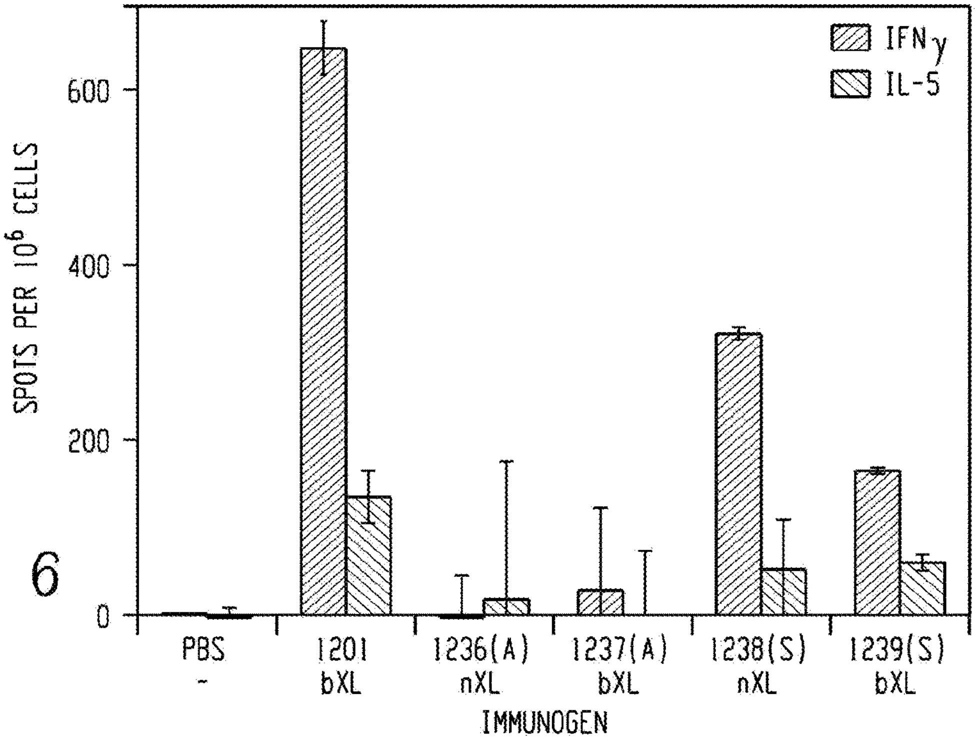
FIG. 6 shows spleen cells harvested on day 59 from C57BL/6J mice immunized with T1BT* microparticle constructs and restimulated with T1B peptide in IFNγ and IL-5 ELISPOT plates.
Figure 7:
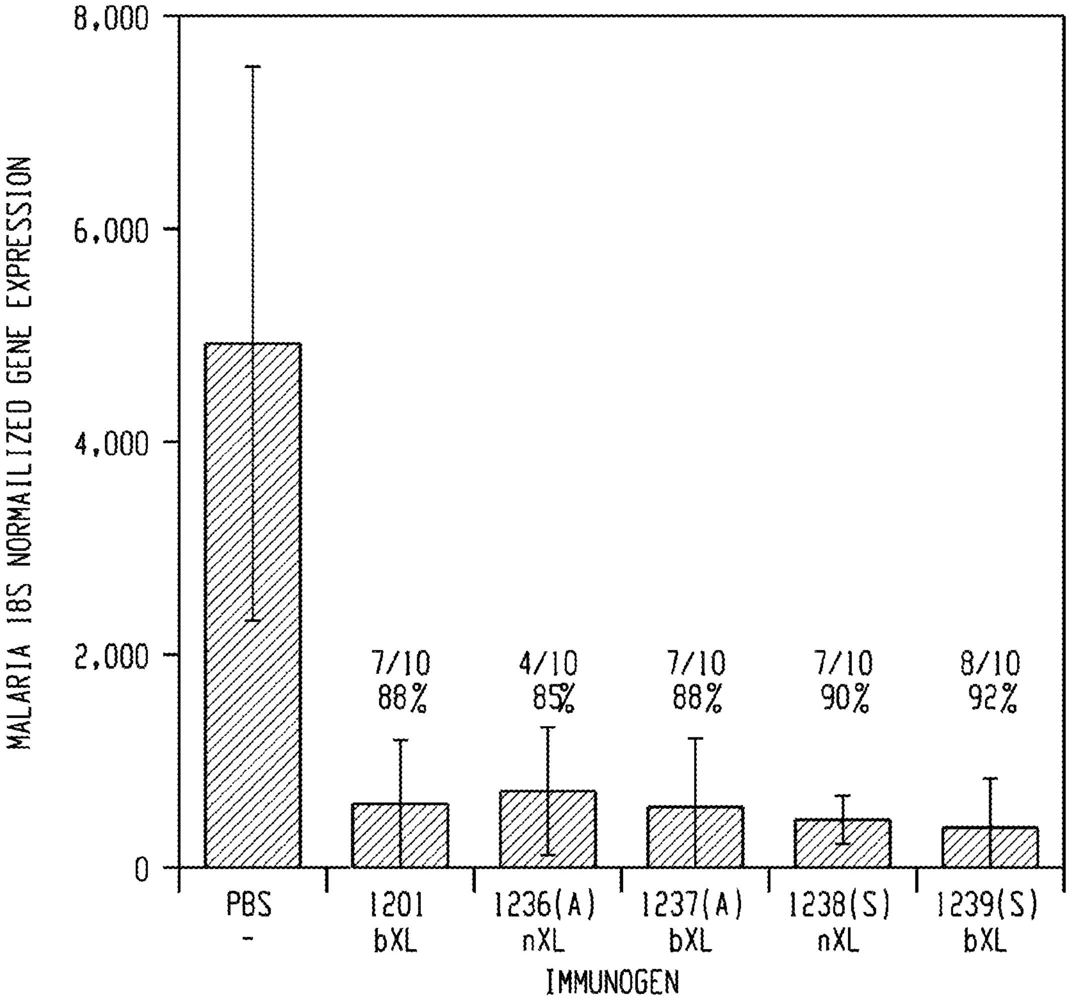
FIG. 7 shows the results for from C57BL/6J mice immunized with T1BT* microparticle constructs and then challenged with PfPb on day 63 and sacrificed 40 hours later. Parasite burden in the livers was measured by qPCR.

In Example 4, T-cells were collected from mice immunized with the vaccine microparticle constructs with modified T* epitopes. When tested in T1B peptide specific T-cell assay, only the constructs with the native cysteine residue or the replacement serine residue elicited robust responses. Cells from mice treated with the alanine substitution constructs yielded poor T-cell responses (FIG. 6). Moreover, when the animals were subjected to challenge with the PbPf hybrid organism, animals immunized with microparticles containing the serine mutant showed increased levels of protection relative to mice immunized with the alanine constructs (FIG. 7). Without being held to theory, it is believed that the serine mutant of the T* peptide preserves important molecular interactions with either the MHC presentation molecule or the T-cell receptor, or both, while the alanine mutant is lacking in one or more interactions. The functional result of the missing interactions is a weaker T-cell specific response and a lower level of protection against the live PfPb organism.

Through the practice of protein crystallography, much has been learned about the MHC-antigen peptide-TCR interaction system. However, accurate prediction of MHC binding peptides from a protein primary sequence has not yet been reduced to an exact science. Thus T-cell epitopes still need to be identified and validated by empirical methods. Likewise, acceptable modifications to an identified T-cell epitope need be tested empirically. An epitope with a single point substitution may retain full immunological activity, or show reduced immunological activity, abolished immunological activity, or increased immunological activity compared to the wild-type native sequence. It is also possible that an epitope with a single point substitution may exhibit activity qualitatively different from the wild-type sequence, such as altering the induced T-cell response between Th1 and Th2 phenotypes. While suitable substitutions can be predicted, they must be tested and validated by empirical methods.

Further disclosed herein is an immunogenic composition, said immunogenic composition comprising a multilayer film comprising two or more layers of polyelectrolytes, wherein adjacent layers comprise oppositely charged polyelectrolytes, wherein one layer comprises a *Plasmodium* protozoan epitope. The immunogenic composition optionally further comprises one or more layers comprising a designed polypeptide.

In one embodiment, an immunogenic composition further comprises a second *Plasmodium* protozoan epitope in addition to the modified T* or modified T1BT* epitope, either on the same or different designed polypeptides. In one embodiment, the immunogenic composition comprises a plurality of unique antigenic polyelectrolytes. In another embodiment, the immunogenic composition comprises a plurality of immunogenic polyelectrolytes comprising multiple *Plasmodium* protozoan epitopes within each polyelectrolyte. An advantage of these immunogenic compositions is that multiple antigenic determinants or multiple conformations of a single linear antigenic determinant can be present in a single synthetic vaccine particle. Such compositions with multiple antigenic determinants can potentially yield antibodies against multiple epitopes, increasing the odds that at least some of the antibodies generated by the immune system of the organism will neutralize the pathogen or target specific antigens on cancer cells, for example.

The immunogenicity of an immunogenic composition may be enhanced in a number of ways. In one embodiment, the multilayer film optionally comprises one or more additional immunomodulatory bioactive molecules. Although not necessary, the one or more additional immunomodulatory bioactive molecules will typically comprise one or more additional antigenic determinants. Suitable additional immunomodulatory bioactive molecules include, for example, a drug, a protein, an oligonucleotide, a nucleic acid, a lipid, a phospholipid, a carbohydrate, a polysaccharide, a lipopolysaccharide, a low molecular weight immune stimulatory molecule, or a combination comprising one or more of the foregoing bioactive molecules. Other types of additional immune enhancers include a functional membrane fragment, a membrane structure, a virus, a pathogen, a cell, an aggregate of cells, an organelle, or a combination comprising one or more of the foregoing bioactive structures.

In one embodiment, the multilayer film/immunogenic composition evokes a response from the immune system to a pathogen. In one embodiment, a vaccine composition comprises an immunogenic composition in combination with a pharmaceutically acceptable carrier. Thus a method of vaccination against a pathogenic disease comprises the administering to a subject in need of vaccination an effective amount of the immunogenic composition.

Pharmaceutically acceptable carriers include, but are not limited to, large, slowly metabolized macromolecules such as proteins, polysaccharides, polylactic acids, polyglycolic acids, polymeric amino acids, amino acid copolymers, inactive virus particles, and the like. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes can also be used as carriers.

A method of eliciting an immune response against a disease or pathogen in a vertebrate (e.g., vaccination) comprises administering an immunogenic composition comprising a multilayer film comprising a *Plasmodium* protozoan epitope. In one embodiment, the polyelectrolyte containing the *Plasmodium* protozoan epitope is in the most exterior or solvent-exposed layer of the multilayer film. The immunogenic composition can be administered via a wide variety of routes including oral, intranasal, intravenous, intramuscular, subcutaneous, intraperitoneal, sublingual, intradermal, pulmonary, or transdermal routes. The immunogenic composition can be administered in a single dose or by multiple doses spread over time to achieve optimal response and protection. Generally, the compositions are administered in a manner compatible with the dosage formulation, and in such amount as will be prophylactically and/or therapeutically effective. Precise amounts of immunogenic composition to be administered depend on the judgment of the practitioner and may be peculiar to each subject. It will be apparent to those of skill in the art that the therapeutically effective amount of an immunogenic composition will depend, inter alia, upon the administration schedule, the unit dose of antigen administered, whether the compositions are administered in combination with other therapeutic agents, and the immune status and health of the recipient. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing.

The immunogenic composition optionally comprises an adjuvant. Adjuvants in general comprise substances that boost the immune response of the host in a non-specific manner. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

It is contemplated that an immune response may be elicited via presentation of any protein or peptide capable of eliciting such a response. In one embodiment, the antigen is a key epitope, which gives rise to a strong immune response to a particular agent of infectious disease, i.e., an immunodominant epitope. If desired, more than one antigen or epitope may be included in the immunogenic composition in order to increase the likelihood of an immune response.

Designed peptides adsorb to the surface of an LBL films by virtue of the electrostatic attraction between the charged surface adsorption regions(s) of the designed peptide and the oppositely charged surface of the film. The efficiency of adsorption will depend largely upon the composition of the surface adsorption region(s). Thus designed peptides with different epitopes but similar surface adsorption regions(s) are expected to adsorb with similar efficiency. To fabricate a film that contains two distinct designed polypeptides each at a 1:1 molar ratio, one can mix the peptides at that molar ratio and deposit them simultaneously at a particular layer. Alternatively, one could deposit each peptide individually at separate layers. The molar ratio of peptides adsorbed will largely mirror that relative concentrations at which they were layered or the number of layering steps during which they were incorporated.

The quantity of designed polypeptides incorporated into an LBL film can be measured in a variety of ways. Quantitative amino acid analysis (AAA) is particularly well suited to this purpose. Films containing DP are decomposed to their constituent amino acids by treatment with concentrated hydrochloric acid (6 M) and heating, typically at 115° C. for 15 hours. The amounts of each amino acid are then measured using chromatographic techniques well known to those skilled in the art. Amino acids that occur in only one of the designed peptides in a film can be used as tracers for that peptide. When designed peptides lack unique amino acids, non-natural amino acids (e.g. aminobutyric acid or homovaline) can be incorporated into designed peptides during synthesis. These tracer amino acids are readily identified during the AAA experiment and can be used to quantitate the amount of peptide in the film.

As used herein, a specific T-cell response is a response that is specific to an epitope of interest, specifically a *Plasmodium* protozoan epitope. A specific T-cell response is manifested by secretion of IFNγ and/or IL-5 by T-cells derived from the immunized hose.

As used herein, a specific antibody response is a response that is specific to an epitope of interest, specifically a *Plasmodium* protozoan epitope as disclosed herein.

As used herein, "layer" means a thickness increment, e.g., on a template for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments. Intermingling, or absence thereof, can be monitored by analytical techniques such as surface potential measurements and X-ray photoelectron spectroscopy.

"Amino acid" means a building block of a polypeptide. As used herein, "amino acid" includes the 20 common naturally occurring L-amino acids, all other natural amino acids, all non-natural amino acids, and all amino acid mimics, for example N-alkyl glycine amino acids, often referred to as peptoids.

"Naturally occurring amino acids" means glycine plus the 20 common naturally occurring L-amino acids, that is, alanine, valine, leucine, isoleucine, serine, threonine, cysteine, methionine, aspartic acid, asparagine, glutamic acid, glutamine, arginine, lysine, histidine, phenylalanine, ornithine, tyrosine, tryptophan, and proline.

"Non-natural amino acid" means an amino acid other than any of the 20 common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the α-carbons of the residue. Consequently, the chemical linkages between monomers in a polypeptoid are not peptide bonds, which can be useful for limiting proteolytic digestion.

"Amino acid sequence" and "sequence" mean a contiguous length of polypeptide chain that is at least two amino acid residues long.

"Residue" means an amino acid in a polymer or oligomer; it is the residue of the amino acid monomer from which the polymer was formed. Polypeptide synthesis involves dehydration, that is, a single water molecule is "lost" on addition of the amino acid to a polypeptide chain.

As used herein "peptide" and "polypeptide" all refer to a series of amino acids connected one to the other by peptide bonds between the alpha-amino and alpha-carboxy groups of adjacent amino acids, and may contain or be free of modifications such as glycosylation, side chain oxidation, or phosphorylation, provided such modifications, or lack thereof, do not destroy immunogenicity. As used herein, the term "peptide" is meant to refer to both a peptide and a polypeptide or protein.

"Designed polypeptide" means a polypeptide that has sufficient charge for stable binding to an oppositely charged surface, that is, a polypeptide that can be deposited into a layer of a multilayer film wherein the driving force for film formation is electrostatics. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. In one embodiment, the ratio of the number of charged residues of the same polarity minus the number of residues of the opposite polarity to the total number of residues in the polypeptide is greater than or equal to 0.2 at pH 7.0. While there is no absolute upper limit on the length of the polypeptide, in general, designed polypeptides suitable for LBL deposition have a practical upper length limit of 1,000 residues. Designed polypeptides can include sequences found in nature such as *Plasmodium* protozoan epitopes as well as regions that provide functionality to the peptides such as charged regions also referred to herein as surface adsorption regions, which allow the designed polypeptides to be deposited into a polypeptide multilayer film.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include α-helix, β-sheet, and β-turn.

"Polypeptide multilayer film" means a film comprising one or more designed polypeptides as defined above. For example, a polypeptide multilayer film comprises a first layer comprising a designed polypeptide and a second layer comprising a polyelectrolyte having a net charge of opposite polarity to the designed polypeptide. For example, if the first layer has a net positive charge, the second layer has a net negative charge; and if the first layer has a net negative charge, the second layer has a net positive charge. The second layer comprises another designed polypeptide or another polyelectrolyte.

"Substrate" means a solid material with a suitable surface for adsorption of polyelectrolytes from aqueous solution. The surface of a substrate can have essentially any shape, for example, planar, spherical, cubic, rod-shaped, or other shape. A substrate surface can be smooth or rough, regular or irregular. A substrate can be a crystal. A substrate can be a bioactive molecule. Substrates range in size from the nanoscale to the macro-scale. Moreover, a substrate optionally comprises several small sub-particles. A substrate can be made of organic material, inorganic material, bioactive material, or a combination thereof. Nonlimiting examples of substrates include silicon wafers; charged colloidal particles, e.g., microparticles of $CaCO_3$ or of melamine formaldehyde; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine-formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "capsule" is a polyelectrolyte film in the form of a hollow shell or a coating surrounding a core. The core comprises a variety of different encapsulants, for example, a protein, a drug, or a combination thereof. Capsules with diameters less than about 1 μm are referred to as nanocapsules. Capsules with diameters greater than about 1 μm are referred to as microcapsules.

"Cross-linking" means the formation of a covalent bond, or several bonds, or many bonds between two or more molecules.

"Bioactive molecule" means a molecule, macromolecule, or complex thereof having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film are a transplanted islet cell, a eukaryotic cell, a bacterial cell, a plant cell, and a yeast cell.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an immunogen is an entity that elicits an immune response.

"Antigen" means a foreign substance that elicits an immune response (e.g., the production of specific antibody molecules) when introduced into the tissues of a susceptible vertebrate organism. An antigen contains one or more epitopes. The antigen may be a pure substance, a mixture of substances (including cells or cell fragments). The term antigen includes a suitable antigenic determinant, auto-antigen, self-antigen, cross-reacting antigen, alloantigen, tolerogen, allergen, hapten, and immunogen, or parts thereof, and combinations thereof, and these terms are used interchangeably. Antigens are generally of high molecular weight and commonly are polypeptides. Antigens that elicit strong immune responses are said to be strongly immunogenic. The site on an antigen to which a complementary antibody may specifically bind is called an epitope or antigenic determinant.

"Antigenic" refers to the ability of a composition to give rise to antibodies specific to the composition or to give rise to a cell-mediated immune response.

As used herein, the terms "epitope" and "antigenic determinant" are used interchangeably and mean the structure or sequence of an antigen that is recognized by an antibody or a T-cell. Examples of epitopes include sequences within proteins and designed polypeptides. Ordinarily an antibody epitope will be on the surface of a protein. A "continuous epitope" is one that involves several or more amino acid residues from a span of linear peptide sequence. A "conformational epitope" involves amino acid residues from discontinuous spans of the linear sequence of a peptide protein that are brought into spatial contact by its three-dimensional fold. A conformational epitope can also be comprised of discontinuous peptide segments from distinct peptides or protein subunits that are brought into spatial contact by subunit quaternary assembly. For efficient interaction to occur between the antigen and the antibody, the epitope must be readily available for binding. Thus, antibody epitopes or antigenic determinants are usually located on a proteins surface or are buried and become surface exposed by a structural rearrangement.

As used herein, a "vaccine composition" is a composition that elicits an immune response when administered to a mammal and that response protects the mammal against subsequent challenge by the immunizing agent or an immunologically cross-reactive agent. Protection can be complete or partial with regard to reduction in symptoms or infection as compared with a non-vaccinated organism. An immunologically cross-reactive agent can be, for example, the whole protein from which a subunit peptide has been derived for use as the immunogen. Alternatively, an immunologically cross-reactive agent can be a different protein, which is recognized in whole or in part by antibodies elicited by the immunizing agent.

As used herein, an "immunogenic composition" is intended to encompass a composition that elicits an immune response in an organism to which it is administered and which may or may not protect the immunized mammal against subsequent challenge with the immunizing agent. In one embodiment, an immunogenic composition is a vaccine composition.

The invention is further illustrated by the following non-limiting examples

EXAMPLES

Testing Protocols

Mice and immunizations: Female C57BL/6J, 6-8 weeks of age, were obtained from Jackson Laboratories and housed at NorthEast Life Sciences, New Haven. Mice were acclimated to the environment for at least one week prior to use. Microparticles were resuspended in PBS to the desired DP concentration (e.g., 10 μg/100 μl/injection) and sonicated for 10 minutes immediately prior to syringe loading and immunization. Mice were immunized with the suspension in the rear footpad on days 0, 21 and 42. Positive control mice were immunized by subcutaneous (s.c.) injection of DP in complete Freund's adjuvant (CFA) on d0 or DP in incomplete Freund's adjuvant (IFA) on days (d21, d42); negative control mice were mock immunized with PBS.

ELISA: Mice were bled on day 49 (post-second boost) and sera were harvested for analysis of antibody responses using ELISA plates coated with T1B peptide. Antibody binding was detected with HRP-labeled goat anti-mouse IgG.

ELISPOT: Mice were sacrificed on day 49 and spleens were harvested and teased into single-cell suspensions that were depleted of erythrocytes by ammonium chloride osmotic shock. Erythrocyte-depleted spleen cells were restimulated with T1B peptide in IFNγ or IL-5 ELISPOT plates using commercial reagents (BD Biosciences) and plates (Millipore Corporation) and following the manufacturers' instructions. The number of spots on each plate was counted in an AID Viruspot Reader.

PfPb challenge: Mice were bled on day 49 and antibody titers were measured by ELISA as described above. Following the antibody measurement, mice were challenged with PfPb (*Plasmodium bergheii* transgenic for the T1BT* subunit of the CS gene of *P. falciparum*). The challenge was accomplished by anesthetizing the mice and allowing PfPb-infected mosquitoes to feed on them for 10 minutes. Two days post-challenge, the challenged mice were bled and sacrificed, and liver RNA was extracted for analysis of parasite burden by qPCR.

Example 1: Exemplary Peptide Design and Synthesis

Figure 12:
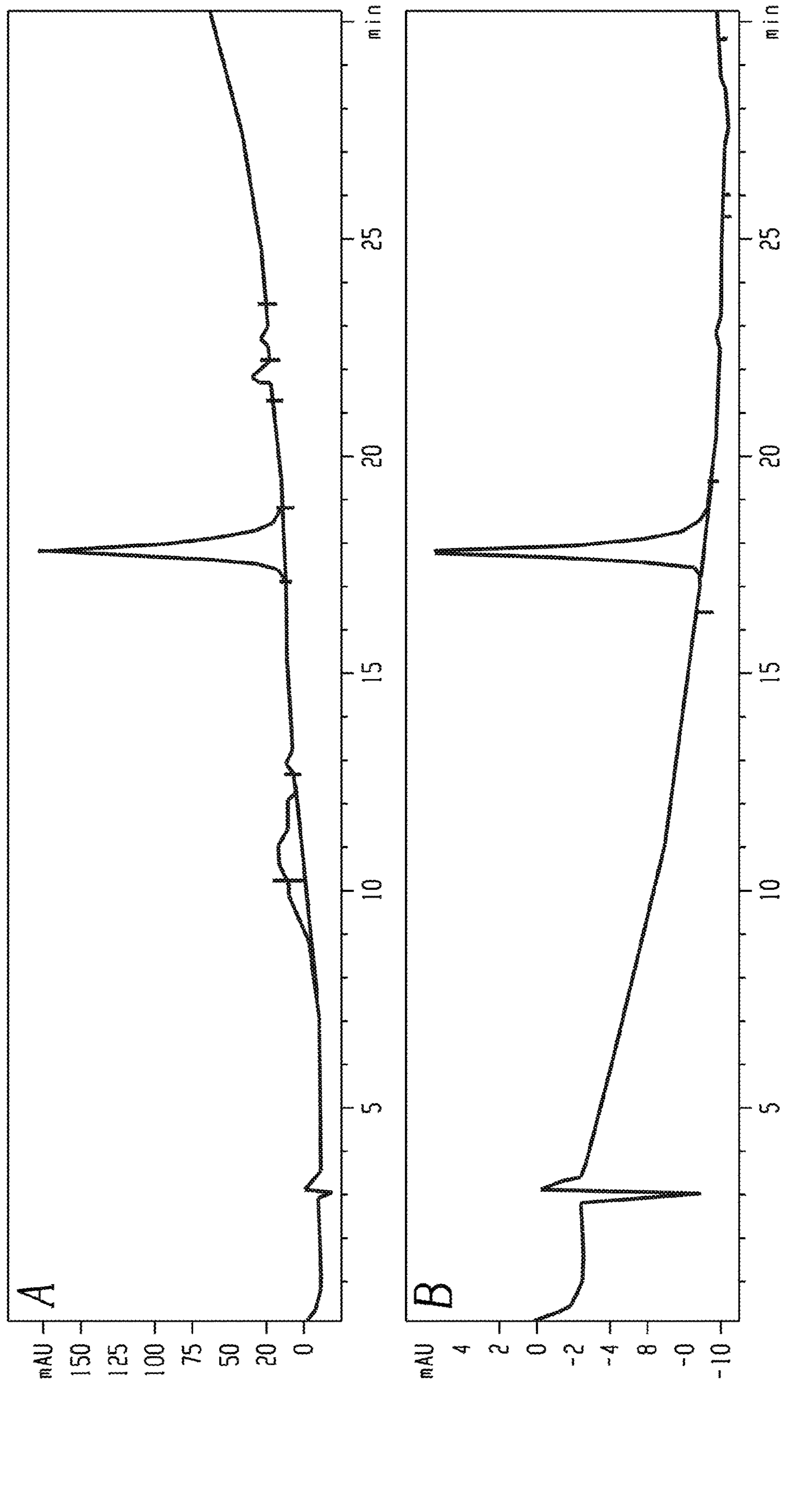
FIG. 12 shows C4 HPLC chromatograms at 214 nm (top) and 280 nm (bottom) for purified Pam3Cys-T1BT*-K20 peptide (SEQ ID NO: 13)
Figure 13:
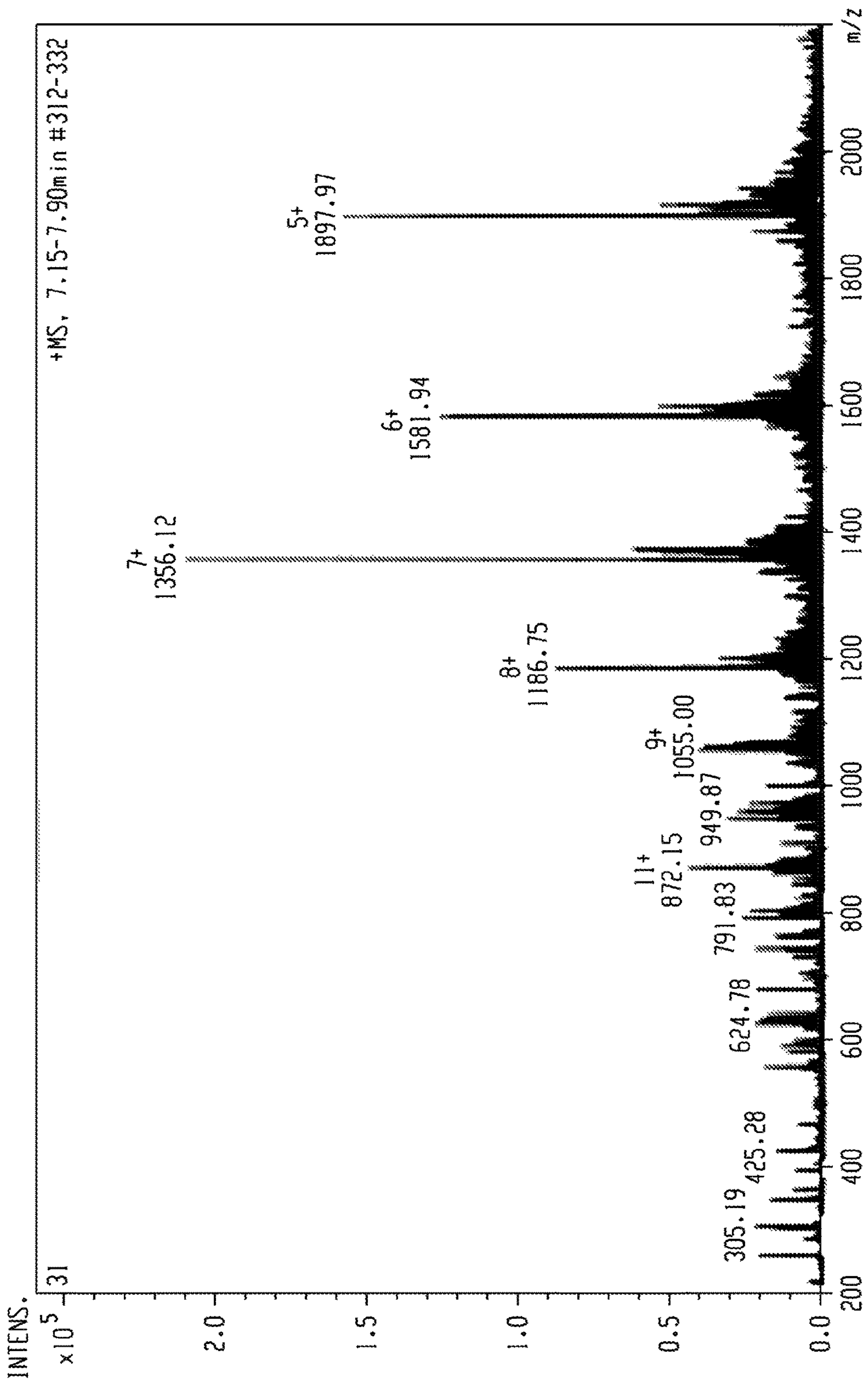
FIG. 13 shows electrospray mass spectrum for purified Pam3Cys-T1BT*-K20 peptide (SEQ ID NO: 13)

Designed polypeptides were based on the T1BT* multivalent peptide of *P. falciparum* CS. The surface adsorption region $K_{20}$ (SEQ ID NO: 9) or $K_{20}Y$ (SEQ ID NO: 16) was added to the C-terminus to yield designed polypeptides (DP) for incorporation in LbL particles (FIG. 1). When Pam3Cys was conjugated to DP, the linker sequence SKKKK was also added. Peptides were synthesized using standard solid phase peptide chemistry procedures and were prepared as C-terminal amides. Briefly, fluorenylmethyloxycarbonyl (Fmoc) amino acids were double coupled to a Rink MBHA amide resin on a CEM Liberty microwave peptide synthesizer using the manufacturer's synthesis protocols with minor modifications to coupling temperatures. Following peptide synthesis, the Pam3Cys group was added to the resin by either manual coupling of Pam3Cys-OH or automated coupling of Fmoc-Pam2Cys-OH followed by Fmoc removal and a final capping step with palmitic acid. Peptides were cleaved from the resin by treatment with a trifluoroacetic acid (TFA)/triisopropylsilane/phenol/water cocktail and precipitated with ether. Crude peptides were purified by C18 HPLC using a water (0.1% TFA)/acetonitrile gradient or by C4 HPLC for Pam3Cys peptides using a water (0.1% TFA)/isopropanol gradient. Purified peptides were quantified by UV absorbance at 280 nm or by amino acid analysis, aliquoted, lyophilized, and stored at −20° C. A typical C4 analytical HPLC chromatogram for SEQ ID NO: 13 is shown in FIG. 12 and electrospray mass spectrum is shown in FIG. 13. Calculated average MW for SEQ ID NO: 13=9486.27. found MW=9485.6.

T1BT*-K20:
(SEQ ID NO: 10)
DPNANPNVDPNANPNVNANPNANPNANPEYLNKIQNSLSTEWSPCSVTSG
NGKKKKKKKKKKKKKKKKKKKKY

Pam3Cys-T1BT*-K20:
(SEQ ID NO: 11)
Pam3CysSKKKKDPNANPNVDPNANPNVNANPNANPNANPEYLNKIQNSL
STEWSPCSVTSGNGKKKKKKKKKKKKKKKKKKKKY

T1BT*-K20 (Cys->Ser):
(SEQ ID NO: 12)
DPNANPNVDPNANPNVNANPNANPNANPEYLNKIQNSLSTEWSPSSVTSG
NGKKKKKKKKKKKKKKKKKKKK

Pam3Cys-T1BT*-K20 (Cys->Ser):
(SEQ ID NO: 13)
Pam3CysSKKKKDPNANPNVDPNANPNVNANPNANPNANPEYLNKIQNSL
STEWSPSSVTSGNGKK

T1BT*-K20 (Cys->Ala):
(SEQ ID NO: 14)
DPNANPNVDPNANPNVNANPNANPNANPEYLNKIQNSLSTEWSPASVTSG
NGKKKKKKKKKKKKKKKKKKKK

Pam3Cys-T1BT*-K20 (Cys->Ala):
(SEQ ID NO: 15)
Pam3CysSKKKKDPNANPNVDPNANPNVNANPNANPNANPEYLNKIQNSL
STEWSPASVTSGNGKKKKKKKKKKKKKKKKKKKK

T1BT*-K20 (Cys->Ser):
(SEQ ID NO: 17)
SKKKKDPNANPNVDPNANPNVNANPNANPNANPEYLNKIQNSLSTEWSPS
SVTSGNGKKKKKKKKKKKKKKKKKKKK

Example 2: LBL Fabrication of Vaccine Microparticles

LBL was performed on a KrosFlo® Research IIi Tangential Flow Filtration System from Spectrum Labs (Rancho Dominiguez, Calif.) equipped with a 20 $cm^2$, 500 kD (MWCO) MicroKros® mPES filter module. Poly-L-glutamate sodium salt (PGA) and poly-L-lysine hydrobromide salt (PLL) were obtained from Sigma-Aldrich, USA (catalog nos. P4636 and P6516, respectively). Spherical, mesoporous $CaCO_3$ cores (2-5 um) were coprecipitated from 0.33 M $CaCl_2$ and 0.33 M $Na_2CO_3$ with 1.0 mg/mL PGA using a modified version of the process reported by Volodkin et al. (D. V. Volodkin et al. *Adv. Funct. Mater.* 2012, 1). All steps were performed at room temperature.

The TFF apparatus was charged with 20 mL of 3% $CaCO_3$ (dry weight) microparticle suspension that was kept in constant circulation at 40 mL/min for the duration of processing. The particles were washed by permeation with 100 mL 10 mM HEPES buffer pH 7.4. The permeate valve was closed and a 5.0 mL aliquot of 6.3 mg/mL PLL was added in a single bolus. The particles were circulated for 5 min, then the permeation valve was opened to concentrate the suspension back to 20 mL volume. The buffer feed valve was opened and the particles were then washed by permeation with 100 mL HEPES buffer. The permeate valve was closed and a 5.0 mL aliquot of 5.0 mg/mL PGA was added in a single bolus. The particles were circulated for 5 min, concentrated, and then washed by permeation with 100 mL HEPES buffer. The previous steps were repeated until a seven layer base film with PGA at the outermost layer was fabricated.

The washed microparticle suspension was removed from the TFF apparatus and base layer film was optionally amide cross-linked (bXL=base layers cross-linked) by treatment with 200 mM EDC and 50 mM sulfo-NHS in 200 mM phosphate buffer, pH 6.5 for 30 min. The particles were pelleted by low speed spin, aspirated, and washed twice with 10 mM HEPES buffer to remove any residual reagent. The microparticles (either nXL or XL) were then immersed in a 0.5 mg/mL solution of the T1BT* DP for 5 min with gentle mixing. Particles were then spun at low speed, and washed with fresh HEPES buffer to provide the final 8 peptide layer microparticle vaccine constructs. The DP loading was measured by quantitative amino acid analysis and then the particles were suspended in HEPES buffer containing 5% mannitol and 0.2% sodium carboxymethylcellulose. The suspension was aliquoted in convenient volumes (e.g. 125 ug total DP), flash frozen in liquid nitrogen, and lyophilized. The resulting dry mannitol cakes were stored at 4° C. and are stable for at least six months.

| Construct | SEQ ID NO: | DP | Epitope | Cross-linked |
|---|---|---|---|---|
| ACT-1198 | 10 | ACT-2062 | T1BT*-K20Y | N |
| ACT-1199 | 11 | ACT-2149 | Pam3C-T1BT*-K20Y | N |
| ACT-1200 | 10 | ACT-2062 | T1BT*-K20Y | Y |
| ACT-1201 | 11 | ACT-2149 | Pam3C-T1BT*-K20Y | Y |
| ACT-1236 | 15 | ACT-2246 | Pam3C-T1BT*-K20 (Cys->Ala) | N |
| ACT-1237 | 15 | ACT-2246 | Pam3C-T1BT*-K20 (Cys->Ala) | Y |
| ACT-1238 | 13 | ACT-2247 | Pam3C-T1BT*-K20 (Cys->Ser) | N |
| ACT-1239 | 13 | ACT-2247 | Pam3C-T1BT*-K20 (Cys->Ser) | Y |

Figure 2:
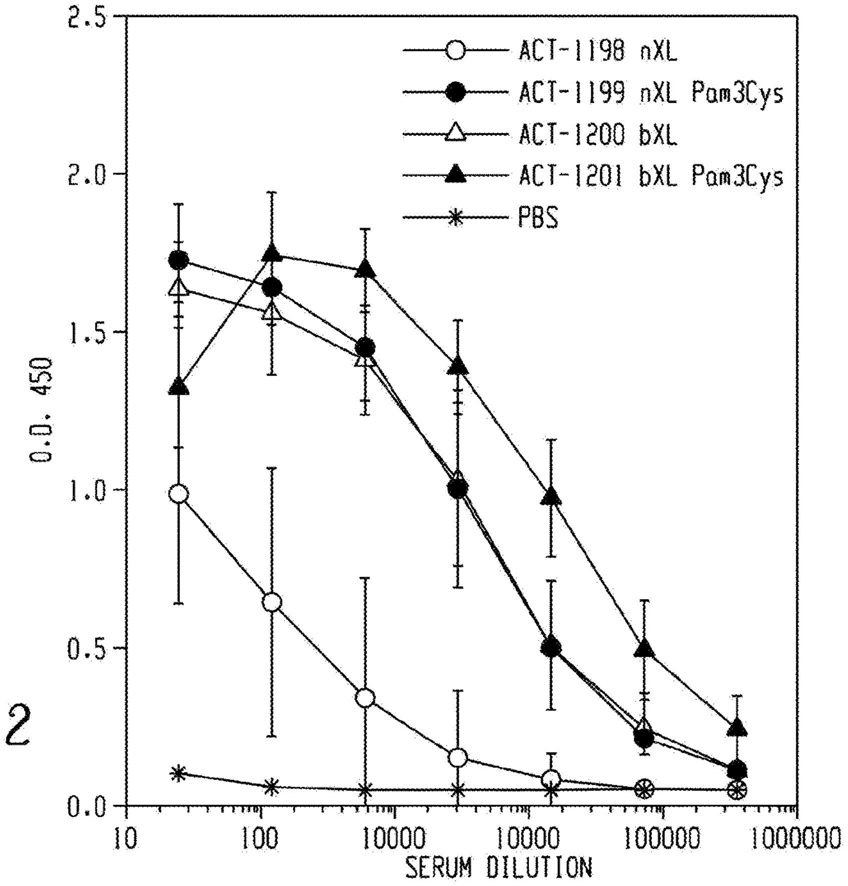
FIG. 2 shows results for sera collected on day 49 from C57BL/6J mice immunized with T1BT* microparticle constructs tested in ELISA against T1B peptide.
Figure 3:
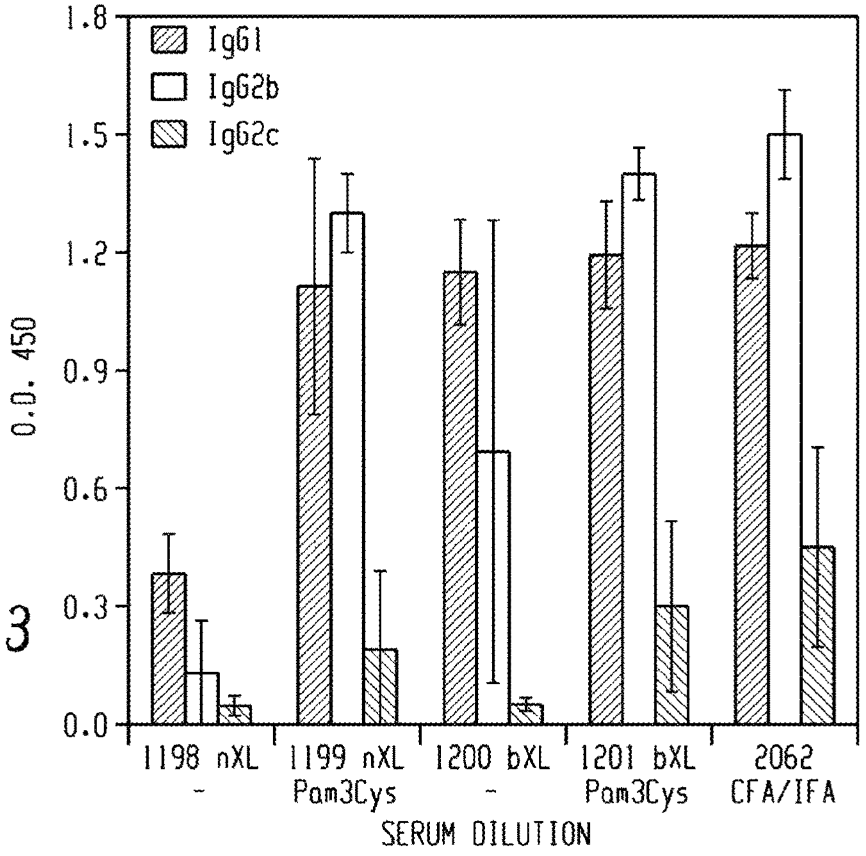
FIG. 3 shows sera from C57BL/6J mice immunized with T1BT* microparticle constructs tested at 1:250, where plates were probed with isotype-specific detection antibodies.
Figure 4:
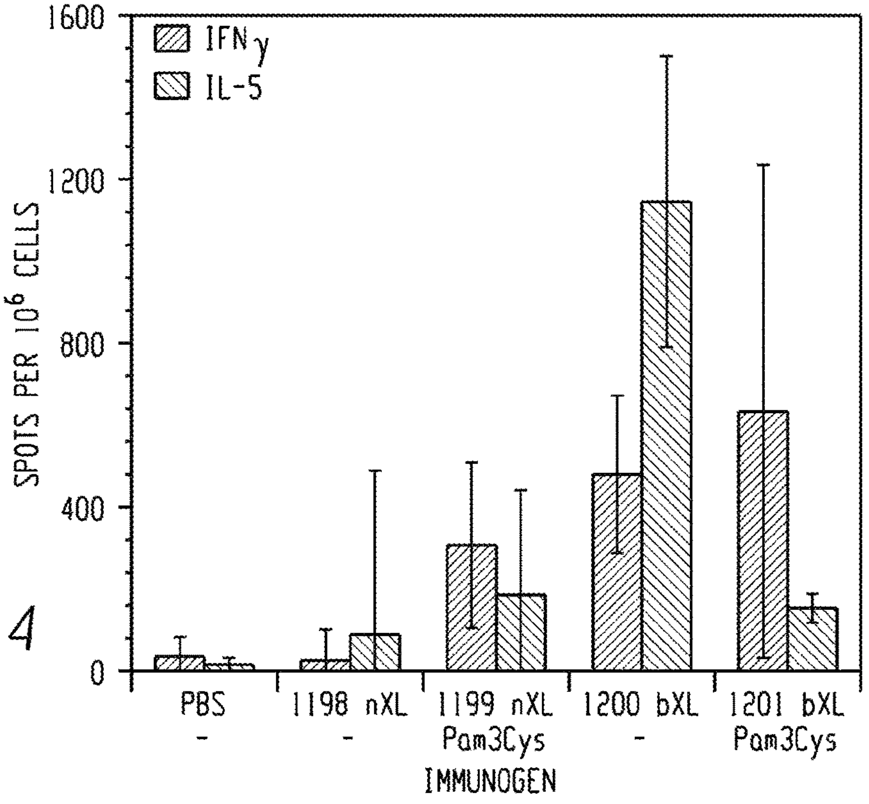
FIG. 4 shows the results for spleen cells harvested on day 49 from C57BL/6J mice immunized with T1BT* microparticle constructs and restimulated with T1B peptide in IFNγ and IL-5 ELISPOT plates.

Example 3: Immune Phenotype Elicited by Immunization with T1BT* Microparticles C57BL/6J mice were immunized with the indicated constructs on day 0, 21 and 42. Sera collected on day 49 were tested in ELISA against T1B peptide as shown in FIG. 2. Results show the mean±SD of 10 mice per group. Sera were tested at 1:250 and plates were probed with isotype-specific detection antibodies as shown in FIG. 3. Results show mean±SD of 10 mice per group. Spleen cells were harvested on day 49 and restimulated with T1B peptide in IFNγ and IL-5 ELISPOT plates as shown in FIG. 4. The data depict the mean±SD of 3 mice per group. nXL=no cross-linking, bXL=base layers cross-linked.

These results demonstrate that LBL microparticles loaded with designed peptide comprising the T1BT* subunit peptide of *P. falciparum* circumsporozoite protein elicit both humoral and cellular immune responses to the included antigenic epitopes. The results further show that modifying the microparticles by cross-linking the base layers increased the potency of the vaccine (higher antibody titers shown in FIG. 2). Modifying the microparticles by including a TLR2 agonist Pam3Cys on the DP also increased their potency but also changed the phenotype of the immune response (increased IgG2c antibody isotype shown in FIG. 3 and decreased IL-5 response shown in FIG. 4). The antibody titers shown in FIG. 2 further demonstrate that inclusion of both modifications in the same microparticle resulted in an additive benefit to the potency of the vaccine.

Example 4: Immunogenicity and Efficacy of T1BT* LbL-MP

Mice were immunized on days 0, 28, and 42 with the indicated constructs. 1236 and 1237 had C→A substitution in T*, while 1238 and 1239 had C→S substitution in T*. Sera were harvested on day 59 and tested in ELISA against T1B peptide as shown in FIG. 5. Results show the mean±SD of 10 mice per group. Spleen cells were harvested on day 59 and restimulated with T1B peptide in IFNγ and IL-5 ELISPOT plates as shown in FIG. 6. The data depict the mean±SD of 3 mice per group. Mice were challenged with PfPb on day 63 and sacrificed 40 hours later as shown in FIG. 7. Parasite burden in the livers was measured by qPCR. Results show mean±SD of 10 mice per group. Insets show # of mice protected (>90% reduction in 18S gene expression compared to PBS control).

These results show that all constructs elicited antibody responses to T1B peptide, but the cross-linking modification again afforded an improvement to the potency of the vaccine. Unexpectedly, ACT-1236 and -1237 (C→A substitution in T*) failed to induce IFNγ and IL-5 T-cell responses to T1B peptide while ACT-1238 and -1239 (C→S substitution in T*) induced both T-cell responses. This difference in activity was surprising since the substitution in these constructs is in the T* epitope which was not present in the ELISPOT assay. There is no reason to expect the C→S substitution to retain activity while the C→A substitution lost activity.

Figure 8:
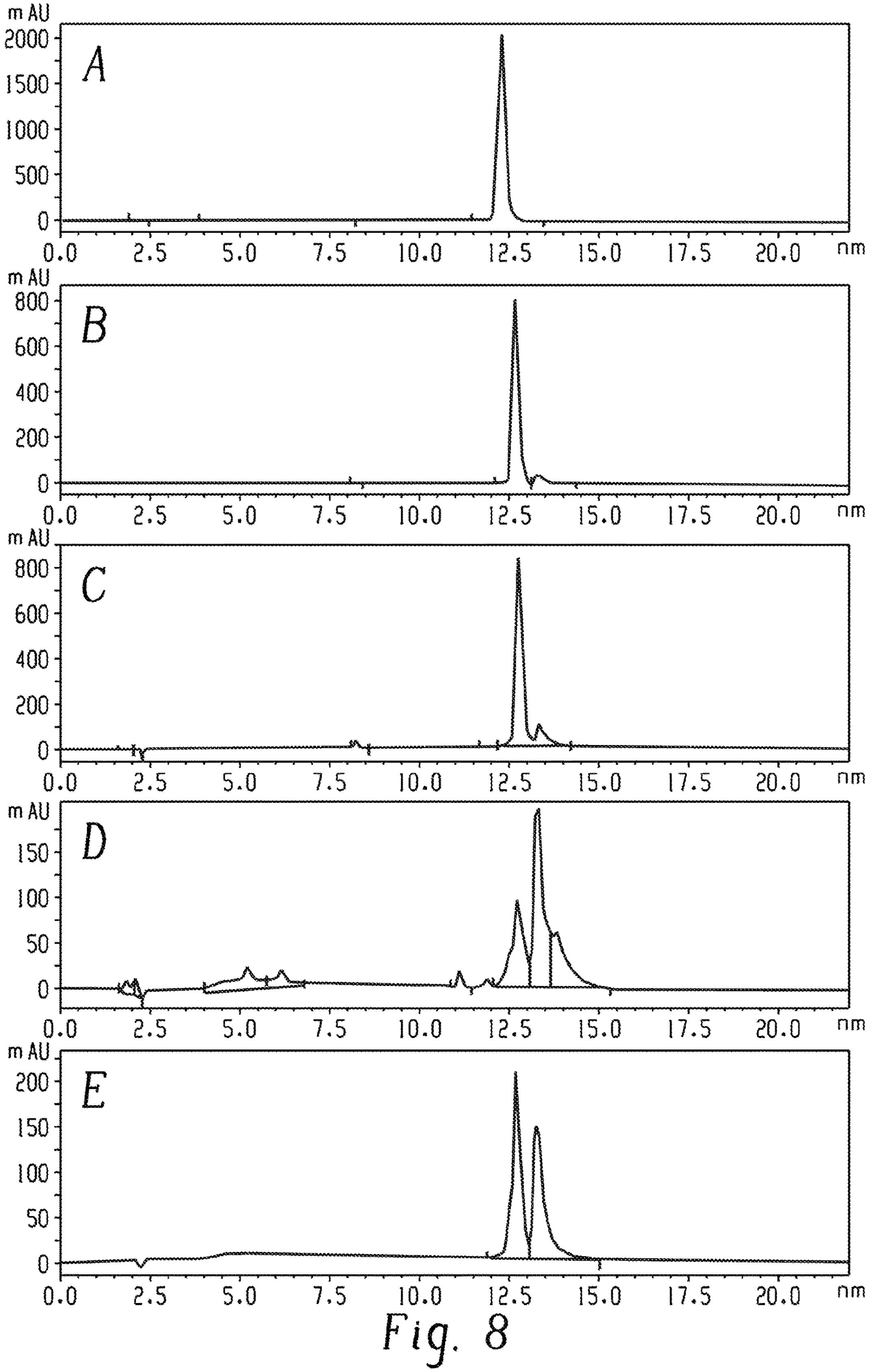
FIG. 8 shows HPLC chromatograms at 214 nm of T1BT*-K20 peptide (SEQ ID NO: 10) after various storage conditions. A) Purified peptide is a single peak. B) After room temperature in pH approximately 5 solution for 16 days. C) After room temperature in pH 7.4 solution for 2.7 days. D) After room temperature in pH 7.4 solution for 16 days. E) After storage at −20° C. as a frozen solution for 4 years.

Example 5: Degradation of Cysteine Containing T1BT* Peptide Under Various Storage Conditions Cysteine containing T1BT* designed peptide SEQ ID NO: 10 was synthesized as described in Example 1 and purified to >95% purity as judged by C18 HPLC (FIG. 8A). Samples were dissolved in water or buffer and stored under the following conditions: room temperature in pH approximately 5 solution for 16 days (FIG. 8B), room temperature in pH 7.4 solution for 2.7 days (8C), room temperature in pH 7.4 solution for 16 days (8D), storage at −20 to −10° C. as a frozen solution for 4 years (8E). Analytical HPLC was performed on these samples using a Waters X-bridge C18 column and a gradient of 100% water/(0.075% trifluoroacetic acid (TFA)) to 50% water/acetonitrile (0.075% TFA) over 20 minutes. The chromatograms show the original monomeric peptide at retention time 12.6 minutes and the appearance of a new peak at 13.3 minutes, which is the presumed disulfide dimer.

Figure 9:
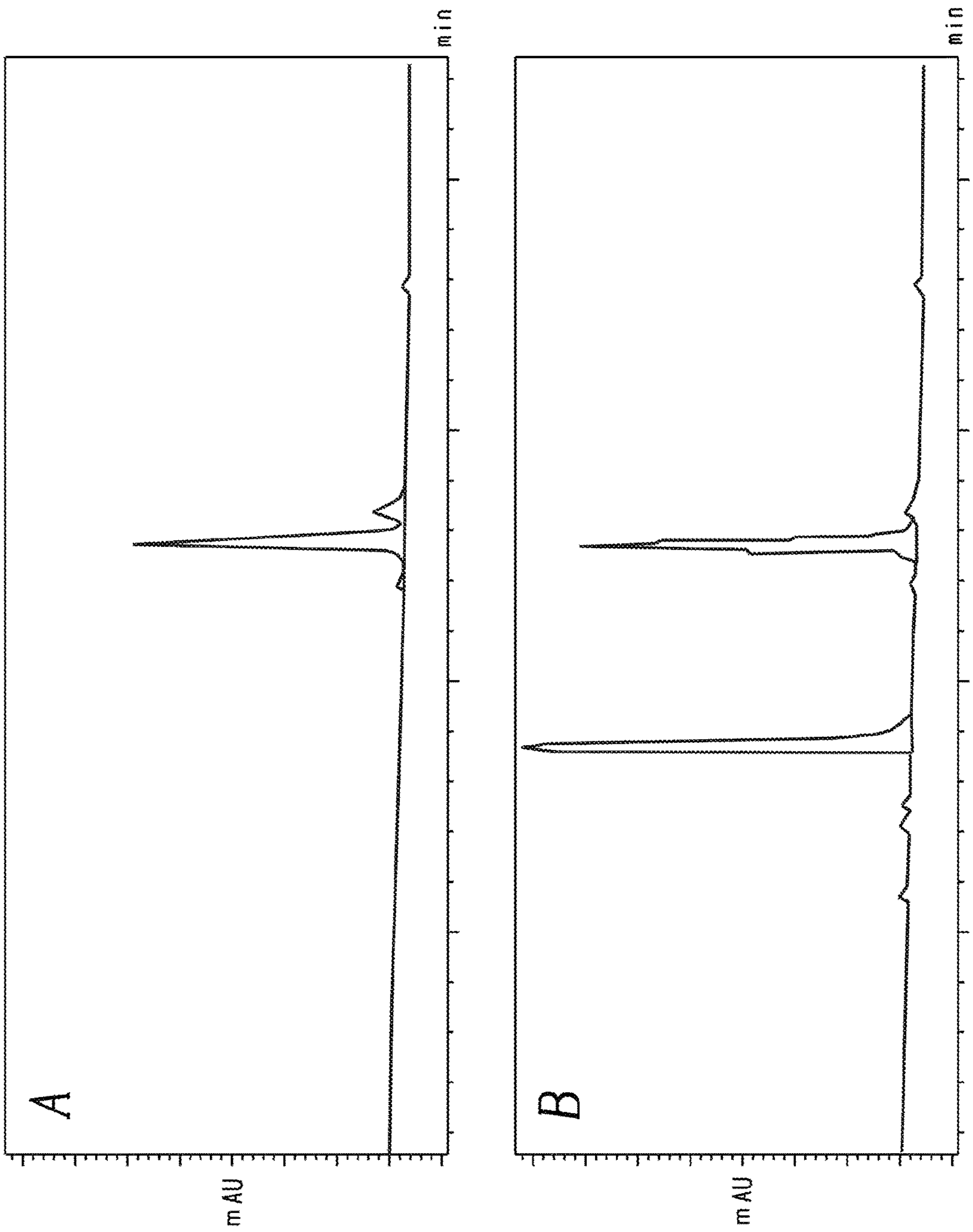
FIG. 9 shows HPLC chromatograms recorded at 280 nm of T1BT*-K20 peptide (SEQ ID NO: 10) mixture. A) After room temperature in approximately pH 5 solution for 16 days. B) After treatment with dithiothreitol.

Example 6: Oxidation of T1BT* Designed Peptide at pH 5 and Reduction with DTT A 1.0 mg/mL solution of T1BT* designed peptide SEQ ID NO: 10 in water was prepared and the pH was estimated by pH paper to be about pH 5. The solution was allowed to sit at room temperature for 16 days after which a second peak with slightly longer retention time appeared in the C18 chromatogram and was presumed to be the disulfide dimer (FIG. 9A). The pH was adjusted to 7.4 by addition of 1 M Tris buffer and a sample was mixed 1:1 with a freshly prepared solution of 1 mg/mL dithiothreitol (DTT). After 5 minutes a second injection on HPLC showed that the later eluting peak was nearly gone, consistent with reduction back to monomer peptide.

Figure 10:
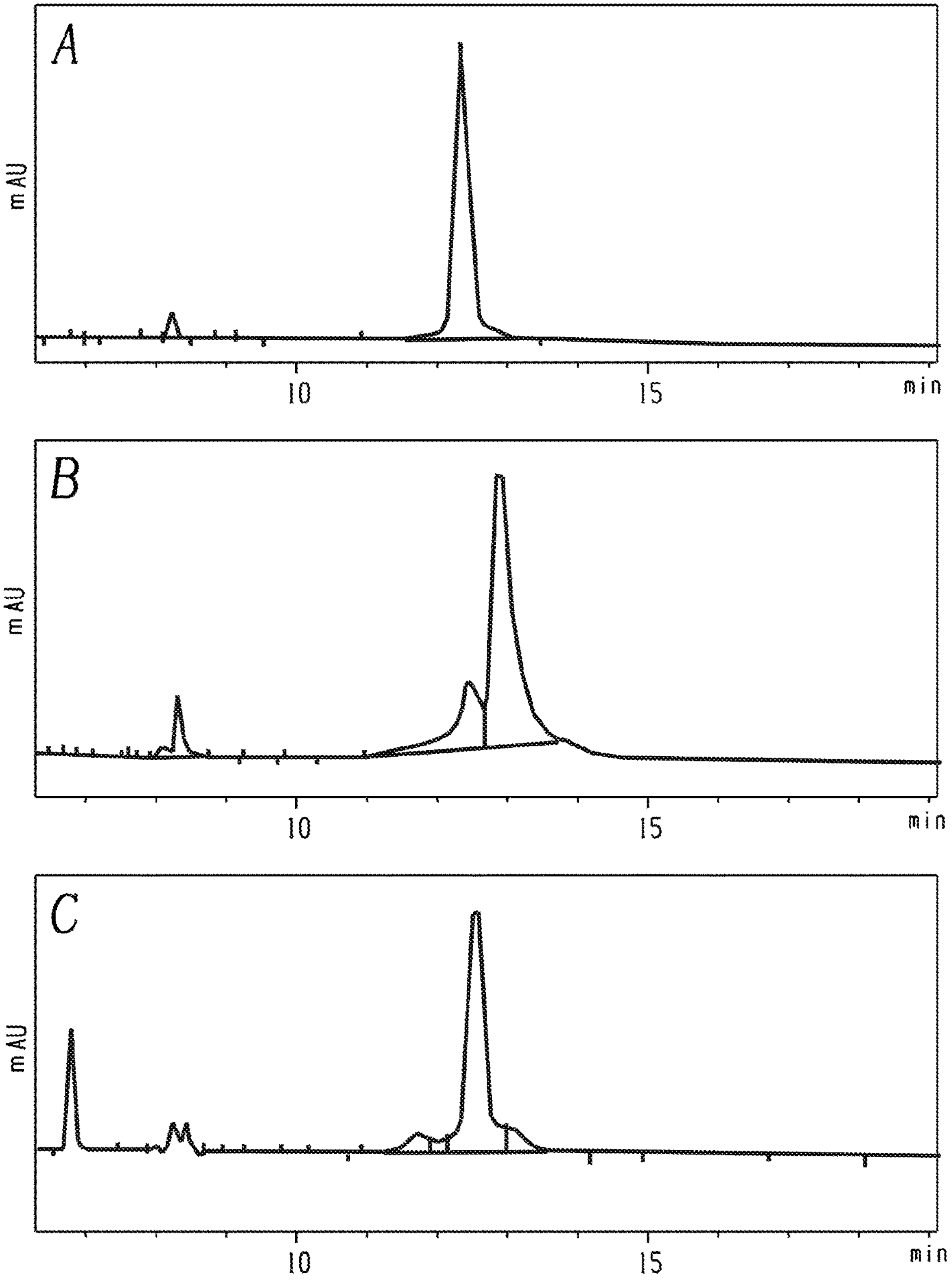
FIG. 10 shows HPLC chromatograms at 214 nm of T1BT*-K20 peptide (SEQ ID NO: 10) mixture. A) Freshly dissolved sample. B) After incubation at room temperature in pH 7.4 solution for 5 days. C) After treatment with dithiothreitol

Example 7: Oxidation of T1BT* Designed Peptide at pH 7.4 and Reduction with DTT A 1.0 mg/mL solution of T1BT* designed peptide SEQ ID NO: 10 in water was prepared and the pH was adjusted to 7.4 by addition of 1 M Tris buffer. The solution was allowed to sit at room temperature for 5 days at which time most of the peptide had converted to dimer as judged by the C18 HPLC chromatogram (FIG. 10B). The sample was then mixed 1:1 with a freshly prepared solution of 1 mg/mL DTT and after 5 min a sample was injected onto HPLC. The chromatogram showed nearly complete conversion back to the monomeric peptide (FIG. 10C).

Example 8: Stability of Serine Containing Designed Peptide SEQ ID NO: 17

Figure 11:
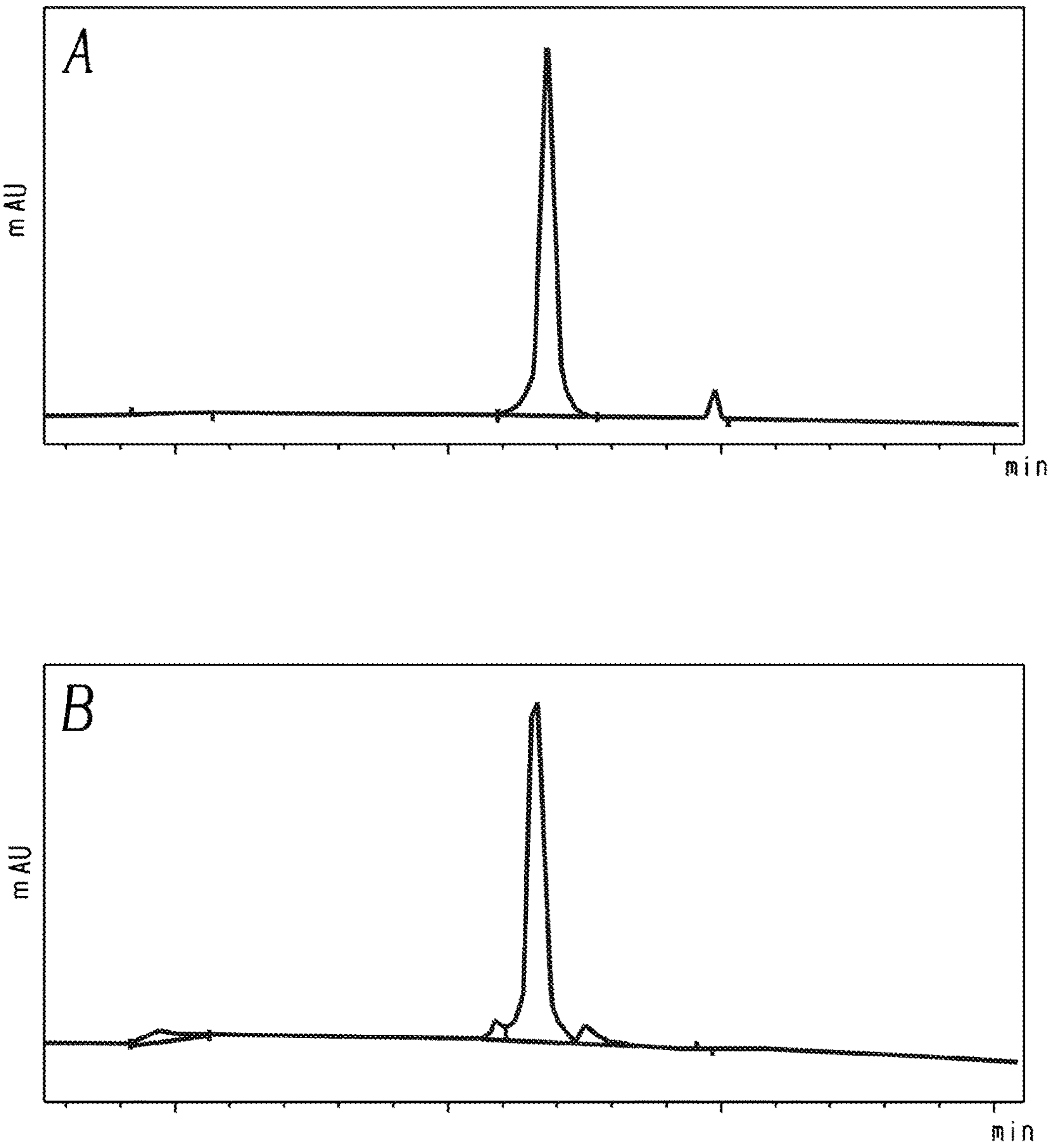
FIG. 11 shows HPLC chromatograms at 214 nm of T1BT*-K20 peptide (SEQ ID NO: 17) mixture. A) Freshly dissolved sample. B) After incubation at room temperature in pH 7.4 solution for 5 days.

A 1.0 mg/mL solution of T1BT* designed peptide SEQ ID NO: 17 in water was prepared and the pH was adjusted to 7.4 by addition of 1 M Tris buffer. The solution was allowed to sit at room temperature for 5 days and monitored by HPLC. The chromatogram shows the appearance of small satellite peaks (FIG. 11B) but most of the designed peptide remained intact, in contrast to the cysteine containing peptide in Example 7.

The use of the terms "a" and "an" and "the" and similar referents (especially in the context of the following claims) are to be construed to cover both the singular and the plural, unless otherwise indicated herein or clearly contradicted by context. The terms first, second, etc., as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 17

<210> SEQ ID NO 1
<211> LENGTH: 16
<212> TYPE: PRT
<213> ORGANISM: Plasmodium falciparum

<400> SEQUENCE: 1

Asp Pro Asn Ala Asn Pro Asn Val Asp Pro Asn Ala Asn Pro Asn Val
1               5                   10                  15


<210> SEQ ID NO 2
<211> LENGTH: 12
<212> TYPE: PRT
<213> ORGANISM: Plasmodium falciparum
```

-continued

<400> SEQUENCE: 2

```
Asn Ala Asn Pro Asn Ala Asn Pro Asn Ala Asn Pro
1               5                   10
```

<210> SEQ ID NO 3
<211> LENGTH: 20
<212> TYPE: PRT
<213> ORGANISM: Plasmodium falciparum

<400> SEQUENCE: 3

```
Glu Tyr Leu Asn Lys Ile Gln Asn Ser Leu Ser Thr Glu Trp Ser Pro
1               5                   10                  15

Cys Ser Val Thr
            20
```

<210> SEQ ID NO 4
<211> LENGTH: 48
<212> TYPE: PRT
<213> ORGANISM: Plasmodium falciparum

<400> SEQUENCE: 4

```
Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Cys Ser Val Thr
        35                  40                  45
```

<210> SEQ ID NO 5
<211> LENGTH: 20
<212> TYPE: PRT
<213> ORGANISM: Artificial Sequence
<220> FEATURE:
<223> OTHER INFORMATION: modified T* epitope

<400> SEQUENCE: 5

```
Glu Tyr Leu Asn Lys Ile Gln Asn Ser Leu Ser Thr Glu Trp Ser Pro
1               5                   10                  15

Ser Ser Val Thr
            20
```

<210> SEQ ID NO 6
<211> LENGTH: 20
<212> TYPE: PRT
<213> ORGANISM: Artificial
<220> FEATURE:
<223> OTHER INFORMATION: modified T* epitope

<400> SEQUENCE: 6

```
Glu Tyr Leu Asn Lys Ile Gln Asn Ser Leu Ser Thr Glu Trp Ser Pro
1               5                   10                  15

Ala Ser Val Thr
            20
```

<210> SEQ ID NO 7
<211> LENGTH: 48
<212> TYPE: PRT
<213> ORGANISM: Artificial Sequence
<220> FEATURE:
<223> OTHER INFORMATION: modified T1BT* epitope

<400> SEQUENCE: 7

-continued

```
Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Ser Ser Val Thr
        35                  40                  45


<210> SEQ ID NO 8
<211> LENGTH: 48
<212> TYPE: PRT
<213> ORGANISM: Artificial Sequence
<220> FEATURE:
<223> OTHER INFORMATION: modified T1BT* epitope

<400> SEQUENCE: 8

Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Ala Ser Val Thr
        35                  40                  45


<210> SEQ ID NO 9
<211> LENGTH: 20
<212> TYPE: PRT
<213> ORGANISM: Artificial Sequence
<220> FEATURE:
<223> OTHER INFORMATION: surface adsorption region

<400> SEQUENCE: 9

Lys Lys Lys Lys Lys Lys Lys Lys Lys Lys Lys Lys Lys Lys Lys Lys
1               5                   10                  15

Lys Lys Lys Lys
            20


<210> SEQ ID NO 10
<211> LENGTH: 73
<212> TYPE: PRT
<213> ORGANISM: Artificial Sequence
<220> FEATURE:
<223> OTHER INFORMATION: designed peptide

<400> SEQUENCE: 10

Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Cys Ser Val Thr
        35                  40                  45

Ser Gly Asn Gly Lys Lys Lys Lys Lys Lys Lys Lys Lys Lys Lys Lys
    50                  55                  60

Lys Lys Lys Lys Lys Lys Lys Lys Tyr
65                  70


<210> SEQ ID NO 11
<211> LENGTH: 84
<212> TYPE: PRT
<213> ORGANISM: Artificial Sequence
<220> FEATURE:
<223> OTHER INFORMATION: designed peptide

<400> SEQUENCE: 11
```

-continued

```
Pro Ala Met Cys Tyr Ser Ser Lys Lys Lys Lys Asp Pro Asn Ala Asn
1               5                   10                  15

Pro Asn Val Asp Pro Asn Ala Asn Pro Asn Val Asn Ala Asn Pro Asn
            20                  25                  30

Ala Asn Pro Asn Ala Asn Pro Glu Tyr Leu Asn Lys Ile Gln Asn Ser
        35                  40                  45

Leu Ser Thr Glu Trp Ser Pro Cys Ser Val Thr Ser Gly Asn Gly Lys
    50                  55                  60

Lys Lys Lys Lys Lys Lys Lys Lys Lys Lys Lys Lys Lys Lys Lys Lys
65                  70                  75                  80

Lys Lys Lys Tyr
```

<210> SEQ ID NO 12
<211> LENGTH: 72
<212> TYPE: PRT
<213> ORGANISM: Artificial Sequence
<220> FEATURE:
<223> OTHER INFORMATION: designed peptide

<400> SEQUENCE: 12

```
Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Ser Ser Val Thr
        35                  40                  45

Ser Gly Asn Gly Lys Lys Lys Lys Lys Lys Lys Lys Lys Lys Lys Lys
    50                  55                  60

Lys Lys Lys Lys Lys Lys Lys Lys
65                  70
```

<210> SEQ ID NO 13
<211> LENGTH: 83
<212> TYPE: PRT
<213> ORGANISM: Artificial Sequence
<220> FEATURE:
<223> OTHER INFORMATION: designed peptide

<400> SEQUENCE: 13

```
Pro Ala Met Cys Tyr Ser Ser Lys Lys Lys Lys Asp Pro Asn Ala Asn
1               5                   10                  15

Pro Asn Val Asp Pro Asn Ala Asn Pro Asn Val Asn Ala Asn Pro Asn
            20                  25                  30

Ala Asn Pro Asn Ala Asn Pro Glu Tyr Leu Asn Lys Ile Gln Asn Ser
        35                  40                  45

Leu Ser Thr Glu Trp Ser Pro Ser Ser Val Thr Ser Gly Asn Gly Lys
    50                  55                  60

Lys Lys Lys Lys Lys Lys Lys Lys Lys Lys Lys Lys Lys Lys Lys Lys
65                  70                  75                  80

Lys Lys Lys
```

<210> SEQ ID NO 14
<211> LENGTH: 72
<212> TYPE: PRT
<213> ORGANISM: Artificial Sequence
<220> FEATURE:
<223> OTHER INFORMATION: designed peptide

<400> SEQUENCE: 14

```
Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Ala Ser Val Thr
        35                  40                  45

Ser Gly Asn Gly Lys Lys Lys Lys Lys Lys Lys Lys Lys Lys Lys Lys
    50                  55                  60

Lys Lys Lys Lys Lys Lys Lys Lys
65                  70


<210> SEQ ID NO 15
<211> LENGTH: 83
<212> TYPE: PRT
<213> ORGANISM: Artificial Sequence
<220> FEATURE:
<223> OTHER INFORMATION: designed peptide

<400> SEQUENCE: 15

Pro Ala Met Cys Tyr Ser Ser Lys Lys Lys Lys Asp Pro Asn Ala Asn
1               5                   10                  15

Pro Asn Val Asp Pro Asn Ala Asn Pro Asn Val Asn Ala Asn Pro Asn
            20                  25                  30

Ala Asn Pro Asn Ala Asn Pro Glu Tyr Leu Asn Lys Ile Gln Asn Ser
        35                  40                  45

Leu Ser Thr Glu Trp Ser Pro Ala Ser Val Thr Ser Gly Asn Gly Lys
    50                  55                  60

Lys Lys Lys Lys Lys Lys Lys Lys Lys Lys Lys Lys Lys Lys Lys Lys
65                  70                  75                  80

Lys Lys Lys


<210> SEQ ID NO 16
<211> LENGTH: 21
<212> TYPE: PRT
<213> ORGANISM: Artificial Sequence
<220> FEATURE:
<223> OTHER INFORMATION: surface adsorption region

<400> SEQUENCE: 16

Lys Lys Lys Lys Lys Lys Lys Lys Lys Lys Lys Lys Lys Lys Lys Lys
1               5                   10                  15

Lys Lys Lys Lys Tyr
            20


<210> SEQ ID NO 17
<211> LENGTH: 77
<212> TYPE: PRT
<213> ORGANISM: Artificial Sequence
<220> FEATURE:
<223> OTHER INFORMATION: designed peptide

<400> SEQUENCE: 17

Ser Lys Lys Lys Lys Asp Pro Asn Ala Asn Pro Asn Val Asp Pro Asn
1               5                   10                  15

Ala Asn Pro Asn Val Asn Ala Asn Pro Asn Ala Asn Pro Asn Ala Asn
            20                  25                  30
```

-continued

```
Pro Glu Tyr Leu Asn Lys Ile Gln Asn Ser Leu Ser Thr Glu Trp Ser
        35                  40                  45

Pro Ser Ser Val Thr Ser Gly Asn Gly Lys Lys Lys Lys Lys Lys Lys
    50                  55                  60

Lys Lys Lys Lys Lys Lys Lys Lys Lys Lys Lys Lys Lys
65                  70                  75
```

The invention claimed is:

1. A composition comprising a multilayer film comprising a plurality of oppositely charged polyelectrolyte layers, wherein one of the polyelectrolyte layers in the multilayer film comprises a first antigenic polyelectrolyte, wherein the first antigenic polyelectrolyte comprises a modified *Plasmodium falciparum* circumsporozoite T* epitope of SEQ ID NO: 5, and wherein the polyelectrolytes in the multilayer film comprise a polycationic material or a polyanionic material having a molecular weight of greater than 1,000 and at least 5 charges per molecule.

2. The composition of claim 1, wherein the first multilayer film is deposited on a core nanoparticle or core microparticle, or is in the form of a nanocapsule or microcapsule prepared by dissolving the core nanoparticle or core microparticle.

3. The composition of claim 1, wherein the modified *Plasmodium falciparum* circumsporozoite T* epitope of SEQ ID NO: 5 is covalently linked to a polycationic material or a polyanionic material having a molecular weight of greater than 1,000 and at least 5 charges per molecule.

4. The composition of claim 1, wherein the modified *Plasmodium falciparum* circumsporozoite T* epitope of SEQ ID NO: 5 is covalently linked to one or two surface adsorption regions at the C-terminus and/or the N-terminus of the polypeptide, wherein at least one of the surface adsorption regions comprises five or more negatively or positively charged amino acid residues.

5. The composition of claim 1, wherein the multilayer film further comprises a toll-like receptor ligand.

6. The composition of claim 5, wherein the toll-like receptor ligand is covalently linked to the first antigenic polyelectrolyte.

7. The composition of claim 1, wherein the first antigenic polyelectrolyte comprises a modified *Plasmodium falciparum* circumsporozoite T1BT* epitope of SEQ ID NO: 7.

8. The composition of claim 7, wherein the modified *Plasmodium falciparum* circumsporozoite T1BT* epitope of SEQ ID NO: 7 is covalently linked to a polycationic material or a polyanionic material having a molecular weight of greater than 1,000 and at least 5 charges per molecule.

9. The composition of claim 7, wherein the modified *Plasmodium falciparum* circumsporozoite T1BT* epitope of SEQ ID NO: 7 is covalently linked to one or two surface adsorption regions at the C-terminus and/or the N-terminus of the polypeptide, wherein at least one of the surface adsorption regions comprises five or more negatively or positively charged amino acid residues.

10. The composition of claim 7, wherein the first antigenic polypeptide is SEQ ID NO: 12 or SEQ ID NO: 13.

11. The composition of claim 1, wherein administration of the composition to a host organism produces an epitope-specific T-cell response, wherein the T-cell response is an IFNγ T-cell response, an IL-5 T-cell response, or both.

12. The composition of claim 1, wherein at least two polyelectrolyte layers of the multilayer film, other than the layer containing the first antigenic polyelectrolyte, are covalently cross-linked.

13. The composition of claim 12, wherein the covalent cross-links are amide bonds involving amino acid side chain functional groups.

* * * * *

UNITED STATES PATENT AND TRADEMARK OFFICE

CERTIFICATE OF CORRECTION

PATENT NO. : 9,968,665 B2
APPLICATION NO. : 15/264035
DATED : May 15, 2018
INVENTOR(S) : James Gorham Boyd and Thomas J. Powell It is certified that error appears in the above-identified patent and that said Letters Patent is hereby corrected as shown below:

In the Specification

Column 22, Line 39, “T1BT*-K20” should read --T1BT*-K20Y--;
Line 44, “Pam3Cys-T1BT*-K20” should read --Pam3Cys-T1BT*-K20Y--;
Line 54, “STEWSPSSVTSGNGKK” should read
--STEWSPSSVTSGNGKKKKKKKKKKKKKKKKKKKK--.

Columns 29-32, SEQ ID NO 11, “<211> LENGTH: 84” should read --<211> LENGTH: 79--;
Replace the first six amino acids “Pro Ala Met Cys Tyr Ser” with --Cys--, and renumber the amino acids;
Insert the following data elements immediately before the data element “<400> SEQUENCE: 11”:
--<220> FEATURE:
<221> NAME/KEY: LIPID
<222> LOCATION: (1)..(1)
<223> OTHER INFORMATION: Pam3--.

Columns 31-32, SEQ ID NO 13, “<211> LENGTH: 83” should read --<211> LENGTH: 78--;
Replace the first six amino acids “Pro Ala Met Cys Tyr Ser” with --Cys--, and renumber the amino acids;
Insert the following data elements immediately before the data element “<400> SEQUENCE: 13”:
--<220> FEATURE:
<221> NAME/KEY: LIPID
<222> LOCATION: (1)..(1)
<223> OTHER INFORMATION: Pam3--.

Columns 33-34, SEQ ID NO 15, “<211> LENGTH: 83” should read --<211> LENGTH: 78--;
Replace the first six amino acids “Pro Ala Met Cys Tyr Ser” with --Cys--, and renumber the amino acids;
Insert the following data elements immediately before the data element “<400> SEQUENCE: 15”:
--<220> FEATURE:

Signed and Sealed this
Seventh Day of May, 2024

Katherine Kelly Vidal

Katherine Kelly Vidal
*Director of the United States Patent and Trademark Office*

<221> NAME/KEY: LIPID
<222> LOCATION: (1)..(1)
<223> OTHER INFORMATION: Pam3--.